(12) United States Patent
Barlaam et al.

(10) Patent No.: US 7,045,539 B2
(45) Date of Patent: May 16, 2006

(54) THERAPEUTIC BENZOXAZOLE COMPOUNDS

(75) Inventors: Bernard Barlaam, Reims (FR); Peter Bernstein, Wilmington, DE (US); Cathy Dantzman, Wilmington, DE (US); Paul Warwick, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/450,927

(22) PCT Filed: Dec. 19, 2001

(86) PCT No.: PCT/SE01/02855

§ 371 (c)(1), (2), (4) Date: Nov. 26, 2003

(87) PCT Pub. No.: WO02/051821

PCT Pub. Date: Jul. 4, 2002

(65) Prior Publication Data

US 2004/0102435 A1 May 27, 2004

(30) Foreign Application Priority Data

Dec. 22, 2000 (SE) .............................................. 0004825
Dec. 22, 2000 (SE) .............................................. 0004826

(51) Int. Cl.
*A61K 31/425* (2006.01)
*C07D 277/62* (2006.01)
*A61P 25/00* (2006.01)

(52) U.S. Cl. ........................ 514/367; 514/375; 548/152; 548/217

(58) Field of Classification Search .................. 548/152, 548/217; 514/367, 375
See application file for complete search history.

(56) References Cited

U.S. PATENT DOCUMENTS

| 5,216,110 A | | 6/1993 | Inbasekaran et al. | |
|---|---|---|---|---|
| 5,665,737 A | * | 9/1997 | Cavalla et al. | ............... 514/338 |
| 6,153,631 A | * | 11/2000 | Petrie et al. | ................. 514/367 |
| 6,420,418 B1 | * | 7/2002 | Hagmann et al. | ............ 514/471 |
| 2002/0133019 A1 | * | 9/2002 | Klunk et al. | ................. 548/156 |

FOREIGN PATENT DOCUMENTS

EP 0483502 A1 6/1995

OTHER PUBLICATIONS

Kimoto et al. 1998, CAS: 128:291486.*

Stevens et al., J. Med. Chem., vol. 37, pp. 1689–1695, 1994.

Bradshaw et al., British Journal of Cancer, vol. 77, No. 5, pp. 745–752, 1998.

Hori et al, Chem. Pharm. Bull., vol. 40, No. 9, pp. 2387–2390, 1995.

Nishi et al, STN International, file CAPLUS, No. 1991:207259, Doc. 114:207259.

* cited by examiner

*Primary Examiner*—Taofiq Solola
*Assistant Examiner*—Robert Shiao
(74) *Attorney, Agent, or Firm*—White & Case LLP

(57) ABSTRACT

Compounds of the formula (I) for use as an estrogen receptor-β-selective ligand are described wherein: X is O or S; and $R^1$, $R^3$ $R^6$ are as described in the specification. The use of these compounds in treating Alzheimer's disease, anxiety disorders, depressive disorders, osteoporosis, cardiovascular disease, rheumatoid arthritis and prostate cancer is described; as are processes for making them.

15 Claims, 2 Drawing Sheets

THERAPEUTIC BENZOXAZOLE COMPOUNDS

TECHNICAL FIELD

Figure 1:
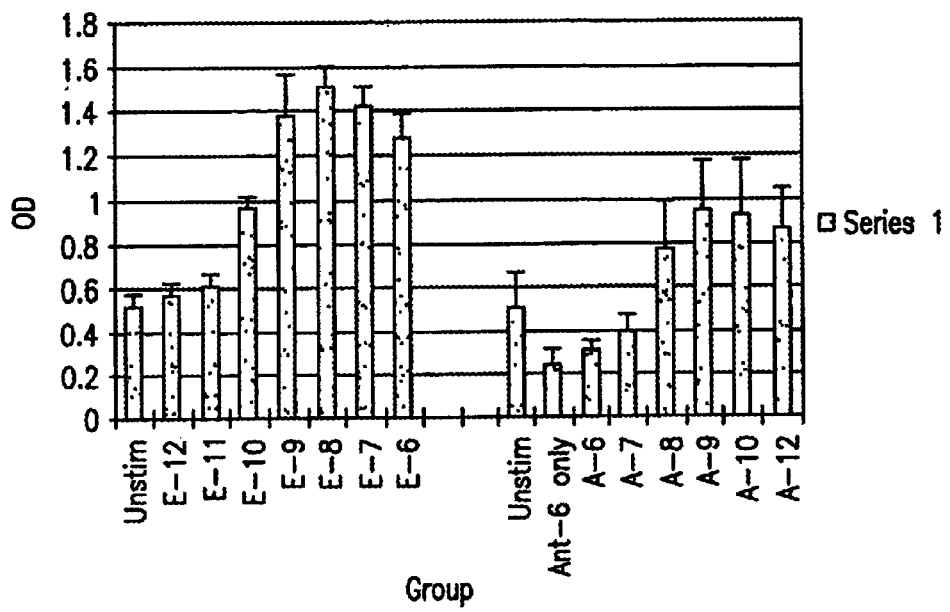
Figure 1:
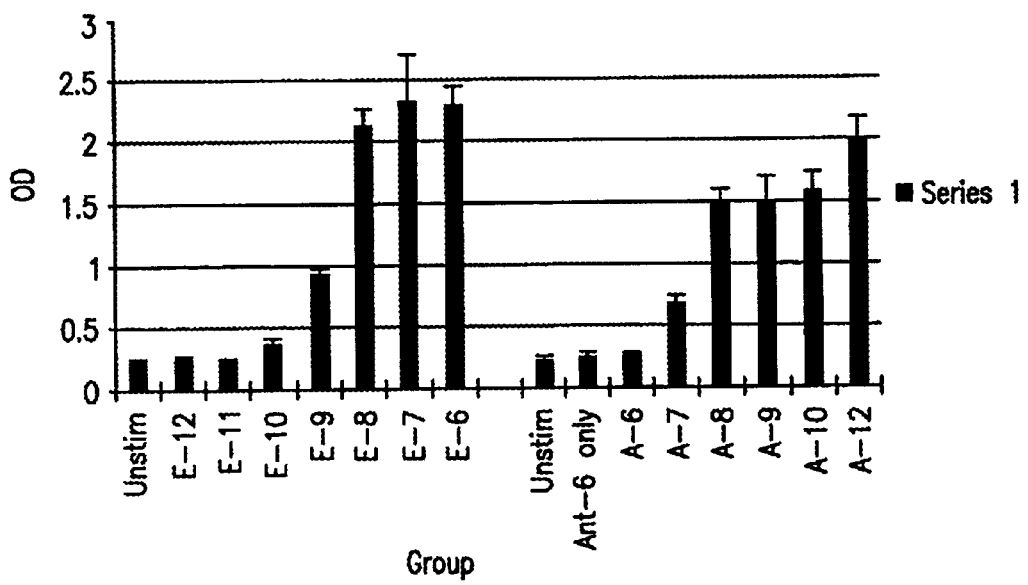

The present invention is directed to a series of ligands, and more particularly to estrogen receptor-β ligands which have better selectivity than estrogen for the estrogen receptor-β over the estrogen receptor-α, as well as to methods for their production and use in the treatment of diseases related to the estrogen receptor-β, specifically, Alzheimer's disease, anxiety disorders, depressive disorders, osteoporosis, cardiovascular disease, rheumatoid arthritis, or prostate cancer.

BACKGROUND

Estrogen-replacement therapy ("ERT") reduces the incidence of Alzheimer's disease and improves cognitive function in Alzheimer's disease patients (Nikolov et al. Drugs of Today, 34(11), 927–933 (1998)). ERT also exhibits beneficial effects in osteoporosis and cardiovascular disease, and may have anxiolytic and anti-depressant therapeutic properties. However, ERT shows detrimental uterine and breast side effects that limit its use.

The beneficial effects of ERT in post-menopausal women is echoed by beneficial effects of estrogen in models relevant to cognitive function, anxiety, depression, bone loss, and cardiovascular damage in ovariectomized rats. Estrogen also produces uterine and breast hypertrophy in animal models reminiscent of its mitogenic effects on these tissues in humans. Specifically, experimental studies have demonstrated that estrogen effects the central nervous system ("CNS") by increasing cholinergic function, increasing neurotrophin/neurotrophin receptor expression, altering amyloid precursor protein processing, providing neuroprotection against a variety of insults, and increasing glutamatergic synaptic transmission, among other effects. The overall CNS profile of estrogen effects in pre-clinical studies is consistent with its clinical utility in improving cognitive function and delaying Alzheimer's disease progression. Estrogen also produces mitogenic effects in uterine and breast tissue indicative of its detrimental side effects on these tissues in humans.

The estrogen receptor ("ER") in humans, rats, and mice exists as two subtypes, ER-α and ER-β, which share about a 50% identity in the ligand-binding domain (Kuiper et al. Endocrinology 139(10) 4252–4263 (1998)). The difference in the identity of the subtypes accounts for the fact that some small compounds have been shown to bind preferentially to one subtype over the other (Kuiper et al.).

In rats, ER-β is strongly expressed in brain, bone and vascular epithelium, but weakly expressed in uterus and breast, relative to ER-α. Furthermore, ER-α knockout (ERKO-α) mice are sterile and exhibit little or no evidence of hormone responsiveness of reproductive tissues. In contrast, ER-β knockout (ERKO-β) mice are fertile and exhibit normal development and function of breast and uterine tissue. These observations suggest that selectively targeting ER-β over ER-α could confer beneficial effects in several important human diseases, such as Alzheimer's disease, anxiety disorders, depressive disorders, osteoporosis, and cardiovascular disease without the liability of reproductive system side effects. Selective effects on ER-β-expressing tissues (CNS, bone, etc.) over uterus and breast could be achieved by agents that selectively interact with ER-β over ER-α.

It is a purpose of this invention to identify ER-β-selective ligands that are useful in treating diseases in which ERT has therapeutic benefits.

It is another purpose of this invention to identify ER-β-selective ligands that mimic the beneficial effects of ERT on brain, bone and cardiovascular function.

It is another purpose of this invention to identify ER-β-selective ligands that increase cognitive function and delay Alzieimer's disease progression.

SUMMARY OF THE INVENTION

This present invention is directed to compounds having the generic structure:

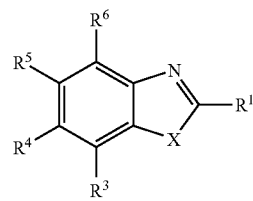

These compounds are ER-β-selective ligands, which mimic ERT, but lack undesirable side effects of ERT and are useful in the treatment or prophylaxis of Alzheimer's disease, anxiety disorders, depressive disorders, osteoporosis, cardiovascular disease, rheumatoid arthritis or prostate cancer.

DETAILED DESCRIPTION OF THE INVENTION

The present invention provides compounds of the formula (I)

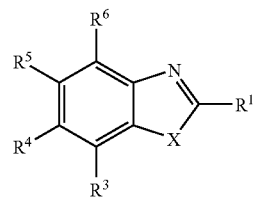

for use as ER-β-selective ligands:
wherein:
X is O or S;
$R^1$ is $C_{1-8}$alkyl, phenyl, benzyl or a 5- or 6-membered ring heterocycle containing 1, 2 or 3 heteroatoms each independently selected from O, N and S and additionally having 0 or 1 oxo groups and 0 or 1 fused benzo rings, wherein the $C_{1-8}$alkyl, phenyl, benzyl or heterocycle is substituted by 0, 1, 2 or 3 substituents selected from —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro and $C_{1-3}$haloalkyl;
$R^3$ is —$R^a$, —$OR^a$, —$SR^a$, —$NR^aR^a$, —$CO_2R^a$, —$OC(=O)R^a$, —$C(=O)NR^aR^a$, —$NR^2C(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro and $C_{1-3}$haloalkyl; or $R^3$ is $C_{1-3}$alkyl containing 1 or 2 substituents selected from —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano and nitro;
$R^4$ is —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS$ (=O)R$^a$, —NR$^a$S(=O)$_2$R$^a$, —C(=O)R$^a$, —S(=O)R$^a$, —S(=O)$_2$R$^a$, halogen, cyano, nitro or C$_{1-3}$haloalkyl;

R$^5$ is —R$^a$, —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro or C$_{1-3}$haloalkyl;

R$^6$ is —R$^a$, —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro and C$_{1-3}$haloalkyl; or R$^6$ is C$_{1-3}$alkyl containing 1 or 2 substituents selected from —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano and nitro; and R$^a$ is H, C$_{1-6}$alkyl, C$_{1-3}$haloalkyl, phenyl or benzyl;

and pharmaceutically acceptable salts thereof.

In the above definitions, where R$^a$ appears twice in a group, each may be separately selected from the possible values.

These compounds are useful in treating disease conditions related to the β-estrogen receptor, more particularly in treating Alzheimer's disease, anxiety disorders, depressive disorders, osteoporosis, cardiovascular disease, rheumatoid arthritis and prostate cancer.

In another aspect the present invention provides the use of a compound of the formula (I) or a pharmaceutically acceptable salt thereof for the manufacture of a medicament for the treatment (including prophylaxis) of disease conditions related to the β-estrogen receptor, more particularly in treating Alzheimner's disease, anxiety disorders, depressive disorders, osteoporosis, cardiovascular disease, rheumatoid arthritis and prostate cancer.

In a further aspect the present invention provides a method of treating disease conditions related to the β-estrogen receptor, more particularly in treating Alzheimer's disease, anxiety disorders, depressive disorders, osteoporosis, cardiovascular disease, rheumatoid arthritis and prostate cancer.

In one embodiment R$^1$ is C$_{1-8}$alkyl, phenyl, benzyl or a 5- or 6-membered ring heterocycle containing 1, 2 or 3 heteroatoms each independently selected from O, N and S and additionally having 0 or 1 oxo groups and 0 or 1 fused benzo rings, wherein the C$_{1-8}$alkyl, phenyl, benzyl or heterocycle is substituted by 0, 1, 2 or 3 substituents selected from —R$^a$, —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro and C$_{1-3}$haloalkyl.

In another embodiment R$^3$ is C$_{1-6}$alkyl, —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro and C$_{1-3}$haloalkyl; or R$^3$ is C$_{1-3}$alkyl containing 1 or 2 substituents selected from —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano and nitro.

In another embodiment R$^4$ is —R$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro or C$_{1-3}$haloalkyl.

In another embodiment R$^5$ is —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro or C$_{1-3}$haloalkyl.

In another embodiment R$^6$ is C$_{1-6}$alkyl, —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro and C$_{1-3}$haloalkyl; or R$^6$ is C$_{1-3}$alkyl containing 1 or 2 substituents selected from —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano and nitro.

In another embodiment R$^1$ is phenyl or benzyl, wherein the phenyl or benzyl is substituted by 0, 1, 2 or 3 substituents selected from —R$^a$, —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro and C$_{1-3}$haloalkyl. In a more specific embodiment, R$^1$ is 4-hydroxyphenyl substituted by 0, 1 or 2 substituents selected from —R$^a$, —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro and C$_{1-3}$haloalkyl.

In one aspect X is S. In another aspect X is O.

R$^1$ may be a 5- or 6-membered ring heterocycle, unsubstituted or substituted as defined hereinabove; for example the 5- or 6-membered ring may be thiophene, furan, pyrrolidinone, pyridine, indazole or thiazolidinone. In a preferred aspect R$^1$ is phenyl unsubstituted or substituted as defined hereinabove. Examples of R$^1$ being substituted phenyl include hydroxyphenyl (for example 4-hydroxyphenyl or 3-hydroxyphenyl), C$_{1-4}$alkoxyphenyl (for example 4-methoxyphenyl or 3-methoxyphenyl), halophenyl (for example bromophenyl such as 2-bromophenyl or chlorophenyl such as 2-chlorophenyl), C$_{1-4}$alkylphenyl (for example methylphenyl such as 2-methylphenyl or 3-methylphenyl or ethylphenyl such as 2-ethylphenyl or propylphenyl such as 2-isopropylphenyl), cyanophenyl (for example 2-cyanophenyl) or trifluoromethylphenyl (for example 4-trifluoromethylphenyl).

In particular R$^1$ is hydroxyphenyl.

In a particular aspect R$^3$ is halo, cyano, carbamoyl or C$_{1-6}$alkyl; more particularly halo for example chloro or bromo, cyano, or C$_{1-6}$alkyl for example methyl or ethyl. In another particular aspect R$^3$ is hydrogen.

In a particular aspect R$^4$ is halo, for example chloro or bromo, hydroxy or C$_{1-6}$alkoxy, for example methoxy or ethoxy; more particularly R$^4$ is hydroxy or methoxy, for example hydroxy. In another particular aspect R$^4$ is hydrogen.

In a particular aspect R$^5$ is halo for example chloro or bromo, hydroxy or C$_{1-6}$ alkoxy for example methoxy or ethoxy; more particularly R$^5$ is hydroxy or methoxy, for example hydroxy. In another particular aspect R$^5$ is hydrogen.

In a particular aspect R$^6$ is halo for example chloro or bromo, C$_{1-4}$alkyl for example methyl or ethyl, trifluoromethyl, hydroxy, C$_{1-4}$alkoxy for example methoxy or ethoxy, carboxy, C$_{1-4}$alkoxycarbonyl for example methoxycarbonyl, cyano, halomethyl for example bromomethyl, cyanoC$_{1-4}$alkyl for example cyanomethyl, carbamoyl, methylcarbamoyl or dimethylcarbamoyl. In another particular aspect R$^6$ is hydrogen. In one embodiment R$^6$ is halo, cyano or C$_{1-6}$alkyl.

Preferred benzoxazoles are there wherein R$^1$ is 4-hydroxyphenyl or 3-chloro-4-hydroxy phenyl; R$^3$ is chloro or bromo; R$^5$ is hydroxy; and R$^4$ and R$^6$ are both hydrogen.

Preferred benzthiazoles are those wherein $R^1$ is 4-hydroxyphenyl; $R^6$ is cyano or carboxy; $R^4$ is hydroxy; and $R^3$ and $R^5$ are both hydrogen.

Compounds within the formula (I) have been disclosed in the literature: J. Med. Chem, 37 (1997) pages 1689–1695; British Journal of Cancer, 77 (1998) pages 745–752; Chem. Pharm. Bull, 40 (1995) pages 2387–2390; EP483502, U.S. Pat. No. 5,216,110 and JP 2306916.

In another aspect the present invention provides compounds of the formula (I) and pharmaceutically acceptable salts thereof with the provisos that when X is S and:
a) R1 is 4-methoxyphenyl, the benzene ring of the benzthiazole is not unsubstituted and is not substituted by 4-methyl, 4,6-dimethoxy, 5-methoxy, 5,6-dimethoxy, 6-methoxy, 6-chloro or 7-methoxy;
b) R1 is 3-methoxyphenyl, the benzene ring of the benzthiazole is not unsubstituted and is not substituted by 6-methoxy;
c) R1 is 3,4-dimethoxyphenyl, the benzene ring of the benzthiazole is not substituted by 6-methoxy, 4,6-dimethoxy or 5,6-dimethoxy;
d) R1 is phenyl, the benzene ring of the benzthiazole is not substituted by 4-methoxy, 5,6-dimethoxy, 6-hydroxy or 6-methoxy;
e) R1 is 4-hydroxyphenyl, the benzene ring of the benzthiazole is not unsubstituted and is not substituted by 4,6-dihydroxy, 5-hydroxy, 5,6-dihydroxy or 6-hydroxy;
f) R1 is 3,4-dihydroxyphenyl, the benzene ring of the benzthiazole is not substituted by 6-hydroxy, 4,6-dihydroxy or 5,6-dihydroxy;
g) R1 is 2-hydroxyphenyl or 3-hydroxyphenyl, the benzene ring of the benzthiazole is not substituted by 6-hydroxy;
h) R1 is 4-methylphenyl, the benzene ring of the benzthiazole is not unsubstituted and is not substituted by 4-, 5- or 6-fluoro, 4-, 6- or 7-methoxy, 5-chloro, 4-, 5-, 6- or 7-hydroxy, 4-, 5-, 6- or 7-acetoxy or 6-nitro;
i) R1 is 3,5-di-tert-butyl-4-hydroxyphenyl, the benzene ring of the benztriazole is not substituted by 4- or 5-hydroxy;
and when X is S, R1 is not 4-aminophenyl, 4-amino-3-methylphenyl or 4-amino-3-halophenyl and when X is S or O, R1 is not 4-chloro- or 4-fluorophenyl when the benzene ring of the benzthiazole is substituted by 5-hydroxy or 5-mercapto.

Particular embodiments, particular aspects and preferred features of the compounds of this invention are as described above for the compounds for use in treating disease conditions related to the β-estrogen receptor.

Particularly useful compounds have any of the above embodiments and also satisfy the equation:

$(K_{i\alpha A}/K_{i\beta A})/(K_{i\alpha E}/K_{i\beta E}) > 100$, wherein $K_{i\alpha A}$ is the $K_i$ value for the agonist in ER-α;
$K_{i\beta A}$ is the $K_i$ value for the agonist in ER-β;
$K_{i\alpha E}$ is the $K_i$ value for estrogen in ER-α; and
$K_{i\beta E}$ is the $K_i$ value for estrogen in ER-β.

Another aspect of the invention is the use of any of the above compound embodiments for the manufacture of a medicament for the treatment or prophylaxis of Alzheimer's disease, anxiety disorders, depressive disorders, osteoporosis, cardiovascular disease, rheumatoid arthritis or prostate cancer.

Another aspect of the invention is the use of any of the above compound embodiments in the treatment or prophylaxis of Alzheimer's disease, anxiety disorders, depressive disorders (including post-partum and post-menopausal depression), osteoporosis, cardiovascular disease, rheumatoid arthritis or prostate cancer.

$C_{Y-Z}$alkyl, unless otherwise specified, means an alkyl chain containing a minimum Y total carbon atoms and a maximum Z total carbon atoms. These alkyl chains may be branched or unbranched, cyclic, acyclic or a combination of cyclic and acyclic. It also includes saturated and unsaturated alkyl such as ethynyl and propenyl. For example, the following substituents would be included in the general description "$C_{4-7}$alkyl":

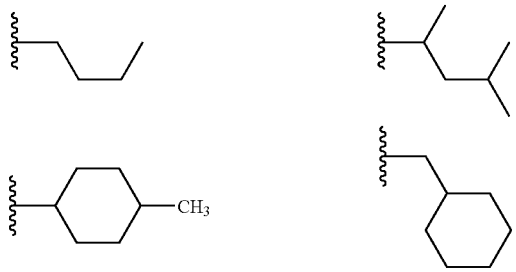

The term "oxo" means a double bonded oxygen (=O).

The compounds of the invention may contain heterocyclic substituents that are 5- or 6-membered ring heterocycles containing 1, 2 or 3 heteroatoms each independently selected from O, N and S and additionally having 0 or 1 oxo groups and 0 or 1 fused benzo rings. A nonexclusive list containing specific examples of such heterocycles are as follows:

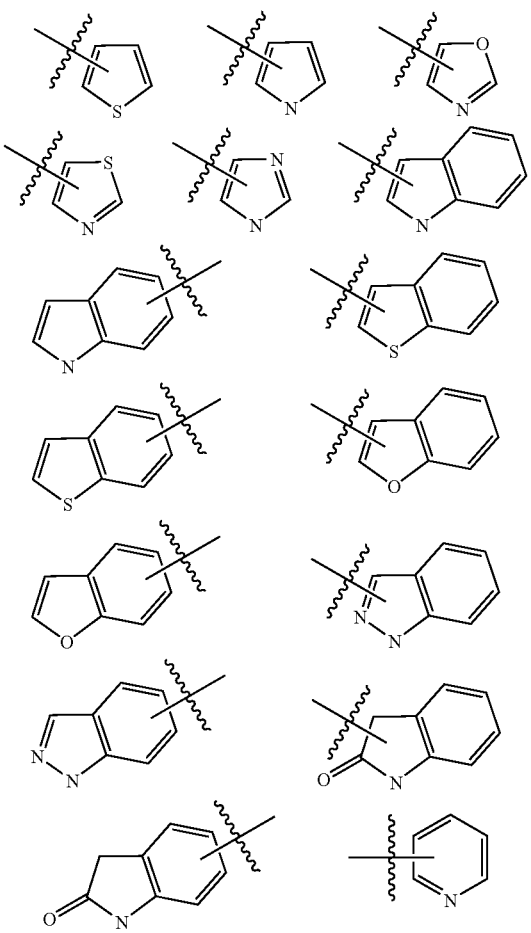

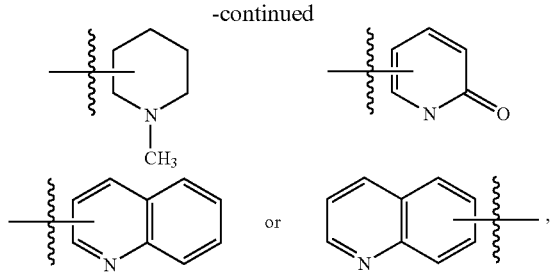

wherein the crossed bond represents that the heterocycle may be attached at any available position on either the heterocycle or the benzo ring.

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethyl-sulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, pamoate, persulfate, phenylacetate, phosphate, picrate, pivalate, propionate, quinate, salicylate, stearate, succinate, sulfamate, sulfanilate, sulfate, tartrate, tosylate (p-toluenesulfonate), and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Estrogen Receptor Binding Measurements

Abbreviated Procedure for Fluorescence Polarization Estrogen Receptor (ERFP) Binding Assay A homogeneous mix-and-measure estrogen receptor (ER) binding assay which utilizes fluorescence polarization (FP) technology is used to identify compounds with affinity for the estrogen receptor. Purchased from PanVera (Madison, Wis.), assay reagents include purified human recombinant ERα, human recombinant ERβ, ES2 screening buffer (100 mM potassium phosphate, pH 7.4, 100 μg/mL bovine gamma globulin), and Fluormone™ ES2. Fluormone™ ES2, whose formulation is proprietary to PanVera, is a fluorescein-tagged, estrogen-like molecule which exhibits approximately equal affinity for ERα and ERβ.

For competition binding experiments, dilutions of test compounds are prepared at 2× the final assay concentration in 0.2% DMSO in ES2 Screening buffer on TECAN Genosys, and 25 μL compound/well is dispensed into black Costar ½ volume 96-well plates. Dependent upon a lot specific $K_d$ determination, 10–40 nM ERα or 10–40 nM ERβ and 1 nM Fluormone ES2 are then added to these plates in a final assay volume of 50 μL/well. Plates are gently shaken for at least 5 minutes to mix and incubated for at least 1 hr 45 minutes to achieve equilibrium. (Reaction mixtures are stable for up to 5 hours). After centrifugation to remove air bubbles, plates are read on an LJL Analyst or Acquest equipped with Criterion software at the following settings: Fluorescence Polarization Mode; Static Polarizer on Excitation Side; Dynamic Polarizer on Emission Side; Excitation λ=485+/−10 nm; Emission λ=520+/−12.5 nm.

Polarized fluorescence intensity values are collected and subsequently converted electronically to millipolarization (mp) values. Following data reduction and normalization with Excel and/or Prism software, % Ctrl values at the various test concentrations are used to obtain $IC_{50}$ values via non-linear regression analysis of a four-parameter logistic equation.

Because ligand depletion is a consideration in this assay (~40–60% input ES2 is bound in the assay), $IC_{50}$ values are converted to $K_i$ values through application of the Kenakin formula, as outlined in the reference below, rather than via the more routinely-used Cheng-Prusoff formula.

Reference: Bolger et al., Rapid Screening of Environmental Chemicals for Estrogen Receptor Binding Capacity, Environmental Health Pespectives:106 (1998), 1–7.

Cell-Based Assay for ER Transcriptional Activity:

ERs are ligand-dependent transcription factors that bind the promoter regions of genes at a consensus DNA sequence called the estrogen responsive element (ERE). The ER agonist or antagonist activity of a drug was determined by measuring the amount of reporter enzyme activity expressed from a plasmid under the control of an estrogen-responsive element when cells transiently transfected with ER and the reporter plasmid were exposed to drug. These experiments were conducted according to the following methods.

Plasmids:

Estrogen Receptors alpha (αER, Gen Bank accession #M12674), and beta (βER, Gen Bank # X99101 were cloned into the expression vector pSG5 (Stratagene) and pcDNA3.1. A trimer of the vitellogenin-gene estrogen response element (vitERE) was synthesized as an oligonucleotide and attached to a beta-globin basal promoter in a construct named pERE3gal. This response element and promoter were removed from pERE3gal by digestion with the endonucleases SpeI (filled with Klenow fragment) and HindIII. This blunt/Hind III fragment was cloned into the β-galactosidase (β-gal) enhancer reporter plasmid (pBGALenh, Stratagene). αER and βER plasmids were purified using a the Endo Free Maxi Kit (Qiagen), and the DNA concentration and purity (A260/280 ratio) were determined spectrophotometrically (Pharmacia). Only DNA with A260/280 ratio of 1.8 and a concentration of >1 ug/uL was used for transfections.

Vitellogenin Response Element Sequence:

*CTAG*TCTCGAGAGGTCACTGTGACCT*AGATCT*  (SEQ ID NO: 1)

AGGTCACTGTGACCTAGATCTAGGTCACTGTGACCTAC

= SpeI overhang

-continued

= XhoI site

= AflII overhang

= ERE consensus

= spacer Bgl II

Cells:

All Transfections are performed in 293 cells (Human Embryonic Kidney cells ATCC # CRL-1573). Cells are grown in DMEM supplemented with 10% FBS, glutamine, sodium pyruvate and penicilin/streptomycin. Cells are grown to 80% confluency and split 1:10 or 1:20.

Transfection:

1. 293T cells are split the night before onto collagen I 150 mm plates (Biocoat Becton Dickinson #354551) at 5 million cells per plate in phenol red-free DMEM (Mediatech 17-205-CV) 10% FBS charcoal stripped (biocell #6201-31) with supplements.
2. The next day the media is changed, 1 hour prior to transfection, to fresh phenol red-free DMEM 10% FBS (charcoal stripped) and supplements.
3. Transfections are performed using the Profection Kit from Promega #E1200, this kit is based on calcium phosphate mediated transfection. Reagents are added in sterile polystyrene tubes in the following order:

Solution A.

20 ug ER alpha or beta (in pcDNA3.1)

50 ug Reporter (pERE3 betaGal)

1.5 ML Sterile Water 186 uL CaCl2

* Mix gently

Solution B 1.5 ml 2×HBSS

4. Using a vortex set on low add solution A to solution B dropwise. The resulting solution should become milky in color. It is important to get thorough mixing at this point. Let solution stand 30 min. Vortex before adding to cells.
5. Add the mixture to 150 mm plates dropwise. Mix well by rocking plates back and forth and side to side gently. View cells under 20× magnification, a very fine precipitate should be seen floating on and above cells after an hour. If you do not observe this the transfection will not work well. Incubate 18–20 hours.

Receptor Stimulation:

6. The day after transfection cells are washed 2× with PBS Ca Mg free containing 1 mM EGTA pH=7.6. Cells are trypsinized for 5 min with 4 ml of trypsin (0.25%)—EDTA. Trypsin is neutralized with 6 ml DMEM (no phenol red)+10% charcoal stripped FBS. Cells are pelleted at 1000×g for 5 min. Cell pellet is resuspended in 10 ml DMEM (no phenol red)+2% charcoal stripped FBS supplemented with glutamine and Penn/Strep and the cells are counted. Additional medium is added to dilute the cell density to 500,000 cells/ml.
7. Cells are plated into 96 well dish (Biocoat BD #354407) at 50 ul of cells per well (=25,000 cells/well), using a multichannel pipettor. Plates are incubated for approx. 2–4 hours to allow cells to attach.
8. Compounds are prepared at concentration of 4 mM in 100% DMSO, then diluted into medium with supplements but no serum. The first 2 dilutions are done in medium with no DMSO, then the remaining dilutions are in medium plus 0.5% DMSO to keep the vehicle constant. Max controls are 10 nM beta-estradiol and background controls are 0.5% DMSO. Compounds are normally tested in the range of 10 uM to 1 nM and are prepared at twice the concentration to be tested. The compounds are added to the cell plates, 50 ul per well. All compounds are tested with an n=4 wells for single poke and n=2 for 9-pt curves.
9. Cells are incubated overnight at 37° C. with the compounds.

Reporter Assay:

1. After 18–24 hr of stimulation, 100 ul of 7% CPRG cocktail is added to each well, the plate is incubated at 37° C. for approximately 30 minutes to 2 hours or until the OD reaches between 1.0 and 2.0. The CPRG (Roche 0884308) will turn bright red as Beta Gal cleaves it.
2. Tie plates are read on a spectrophotometric plate reader (Spectramax, Molecular Devices) at 570 nm and raw absorbances are obtained.

Data is compiled and interpreted with Excel using XLFit or GraphPad Prism to fit concentration-response curves. The EC50 is defined as the concentration at which 50% of the fitted maximum for a compound has been reached.

10×Z Buffer

| Sodium Phosphate (dibasic) 1.7 g | 600 mM |
|---|---|
| Sodium Phosphate (monobasic) 0.96 g | 400 mM |
| Potassium Chloride 149 mg | 100 mM |
| Magnesium Sulfate 0.2 mL of 1 molar stock | 100 mM |
| BME 0.78 mL | 500 mM |

Bring Final Volume to 20 mL with De-Ionized Water

7% CPRG Cocktail

Figure 2:
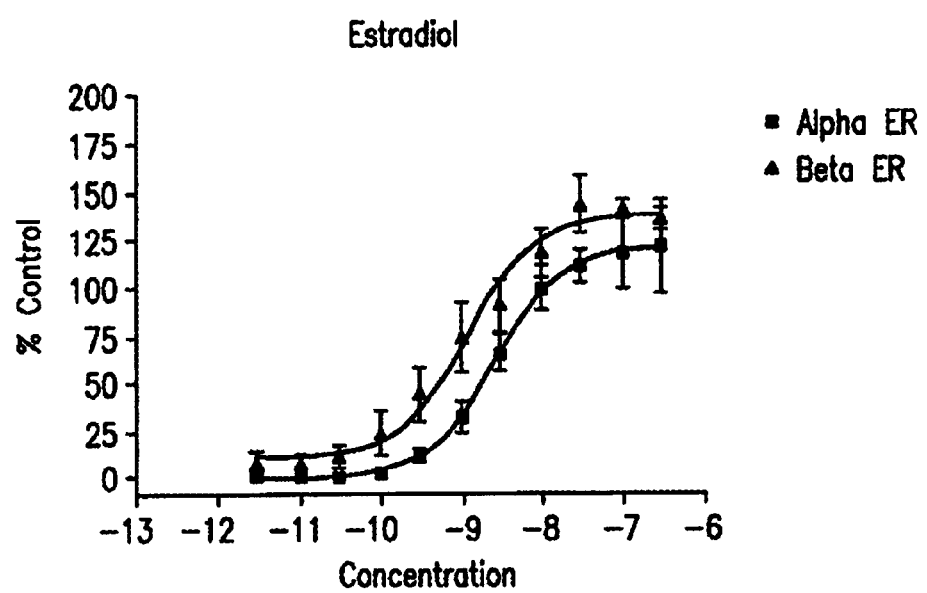

For 50 mLs:

add 3.5 mL of 50 ml of CPRG add 3.5 mL of 10×Z Buffer add 1 mL of 10% SDS bring to 50 mL with DI water Typical Results:

Absorbance values illustrating typical concentration-response curves obtained for the ER agonist 17-β-estradiol (E) and the ER antagonist ICI182,780 (A) are plotted below for cells transfected with either αER or βER, see FIG. 1; or FIG. 2.

Administration and Use

Compounds of the present invention are shown to have high selectivity for ER-β over ER-α, and may possess agonist activity on ER-β without undesired uterine effects. Thus, these compounds, and compositions containing them, may be used as therapeutic agents in the treatment of various CNS diseases related to ER-β, such as, for example, Alzheimer's disease.

The present invention also provides compositions comprising an effective amount of compounds of the present invention, including the nontoxic addition salts, amides and esters thereof, which may, serve to provide the above-recited therapeutic benefits. Such compositions may also be provided together with physiologically-tolerable liquid, gel or solid diluents, adjuvants and excipients. The compounds of the present invention may also be combined with other compounds known to be used as therapeutic agents for the above or other indications.

These compounds and compositions may be administered by qualified health care professionals to humans in a manner similar to other therapeutic agents and, additionally, to other mammals for veterinary use, such as with domestic animals. Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories maybe formed from mixtures containing the active ingredient. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders.

In addition to the compounds of the present invention that display ER-β activity, compounds of the present invention can also be employed as intermediates in the synthesis of such useful compounds.

Synthesis

Compounds within the scope of the present invention may be synthesized chemically by means well known in the art. The following Examples are meant to show general synthetic schemes, which may be used to produce many different variations by employing various commercially available starting materials. These Examples are meant only as guides on how to make some compounds within the scope of the invention, and should not be interpreted as limiting the scope of the invention.

In another aspect, the present invention provides a process for preparing the compounds of the formula (I) and pharmaceutically acceptable salts thereof, which comprises:

a) cyclising a compound of the formula:

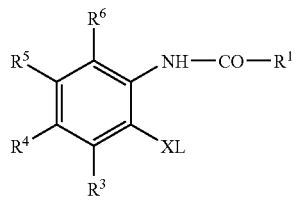

wherein X, $R^1$, $R^3$—$R^6$ are as defined hereinabove and L is hydrogen or a leaving group; or b) for preparing compounds wherein X is O, cyclising a compound of the formula:

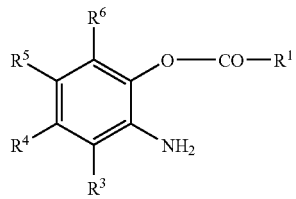

wherein $R^1$, $R^3$—$R^6$ are as defined hereinabove or:

c) cyclising a compound of the formula:

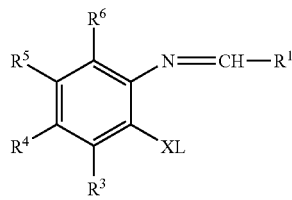

wherein X, $R^1$, $R^3$—$R^6$ are as defined hereinabove and L is hydrogen or a leaving group; or d) for preparing compounds wherein X is S, cyclising a compound of the formula:

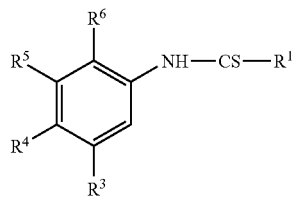

wherein $R^1$, $R^3$—$R^6$ are as defined hereinabove;

and thereafter, if necessary:

i) forming a pharmaceutically acceptable salt;
ii) converting a compound of the formula (I) into another compound of the formula (I).

EXAMPLES

| Example | Structure | Synthetic Method | HPLC (min) | MS (MH+) |
|---|---|---|---|---|
| 1 | 4-Cl, 6-OH benzoxazole-2-(4-hydroxyphenyl) | A, B, C | 1.99 | 262 |
| 2 | 4-Cl, 6-OMe benzoxazole-2-(4-hydroxyphenyl) | A, B | | 276 |
| 3 | 4-Me, 6-OH benzoxazole-2-(4-hydroxyphenyl) | B, C | | 242 |
| 4 | 4-Me, 6-OMe benzoxazole-2-(4-hydroxyphenyl) | B | | 256 |
| 5 | 4-OH, 6-OH benzoxazole-2-(4-hydroxyphenyl) | | | 244 |
| 6 | 6-OH benzoxazole-2-(4-hydroxyphenyl) | B | | 228 |
| 7 | 5-OH benzoxazole-2-(4-hydroxyphenyl) | B, C | | 226 (M − H−) |
| 8 | 5-OMe benzoxazole-2-(4-hydroxyphenyl) | B | | 242 |
| 9 | 4-Cl, 6-OH benzoxazole-2-(2-chloro-4-hydroxyphenyl) | D, E, F, G, H, I | 2.32 | 296 |
| 10 | 4-Br, 6-OH benzoxazole-2-(4-hydroxyphenyl) | F, G, H, I, J | 2.29 | 308 |

-continued
| Example | Structure | Synthetic Method | HPLC (min) | MS (MH+) |
|---|---|---|---|---|
| 11 | 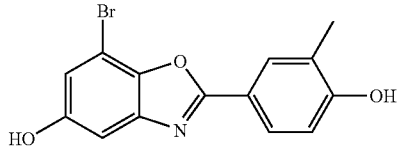 | F, G, H, I, J | 2.18 | 321 |
| 12 | 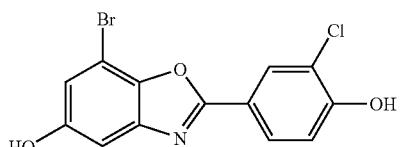 | F, G, H, I, J | 2.30 | 341 |
| 13 | 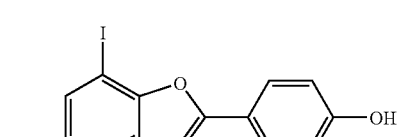 | F, G, H, I, J, K | 2.26 | 354 |
| 14 | 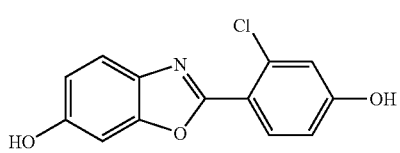 | D, E, G, H, I | 2.07 | 262 |
| 15 | 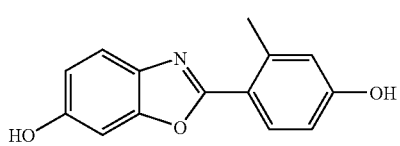 | G, H, I | 2.03 | 242 |
| 16 | 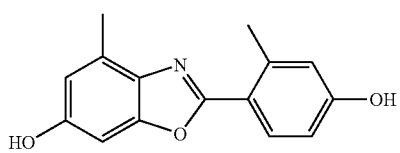 | Ref. 1, F, G, H, I | 2.25 | 256 |
| 17 | 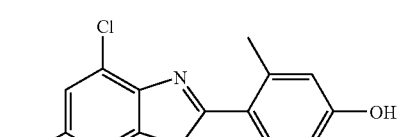 | Ref. 1, F, G, H, I | 2.36 | 276 |
| 18 | 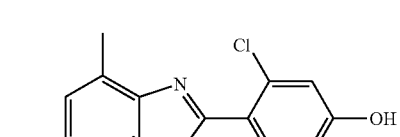 | Ref. 1, D, E, F, G, H, I | 2.02 | 276 |
| 19 | 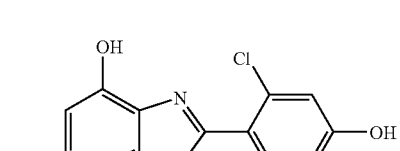 | D, E, F, G, H, I | 2.17 | 278 |

-continued
| Example | Structure | Synthetic Method | HPLC (min) | MS (MH+) |
|---|---|---|---|---|
| 20 | 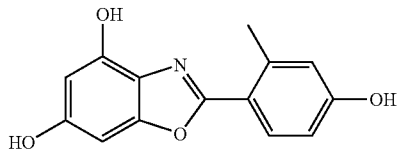 | F, G, H, I | 1.82 | 258 |
| 21 | 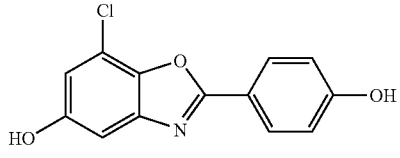 | J, F, G, H, K, L, I | 2.89 | 290 |
| 22 | 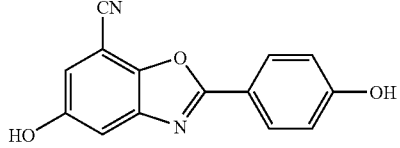 | J, F, G, H, M, I | 253 | 2.06 |
| 23 | 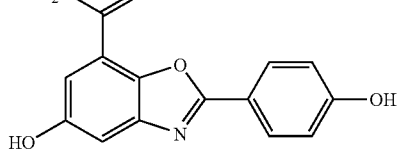 | J, F, G, H, M, I | 2.04 | 271 |
| 24 | 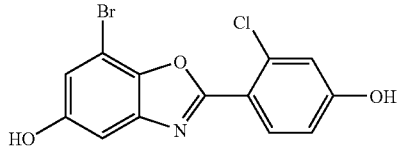 | D, E, J, F, G, H, I, | 2.30 | 341 |
| 25 | 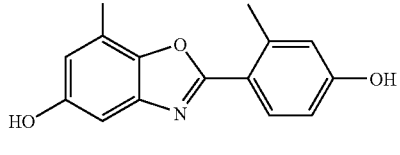 | J, F, G, H, I | 2.32 | 322 |
| 26 | 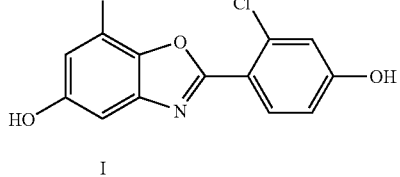 | D, E, J, F, G, H, K, I | 2.24 | 388 |
| 27 | 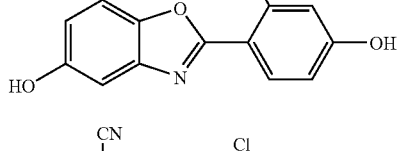 | J, F, G, H, K, I | 2.22 | 368 |
| 28 | 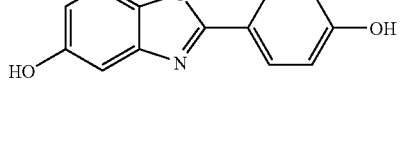 | D, E, J, F, G, H, I, M | 2.05 | 287 |

| Example | Structure | Synthetic Method | HPLC (min) | MS (MH+) |
|---------|-----------|------------------|------------|----------|
| 29 | 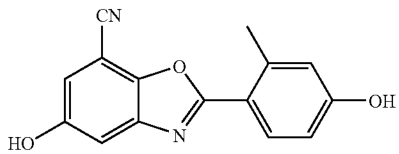 | J, F, G, H, K, I, M | 2.02 | 267 |
| 30 | 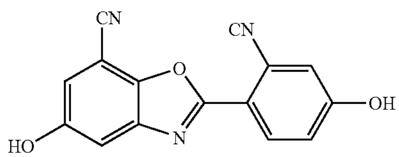 | D, E, J, F, G, H, I, O | 1.92 | 278 |
| 31 | 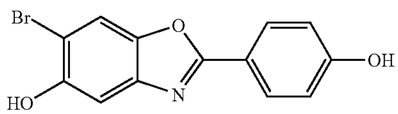 | P, F, G, H, I | 2.18 | 308 |
| 32 | 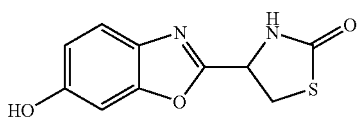 | Q, R, I | 1.20 | 237 |
| 33 | 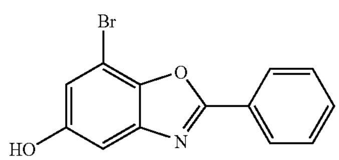 | C | 2.44 | 290.3, 292.3 |
| 34 | 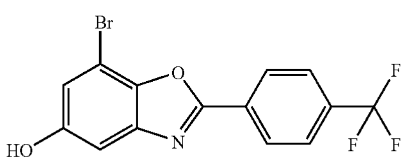 | J, F, Q, R, I | 2.69 | 359 |
| 35 | 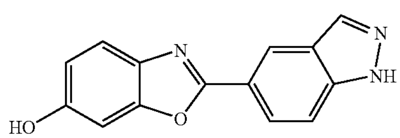 | B | 1.80 | 252.4 |
| 36 | 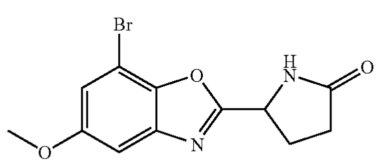 | | 1.84 | 352.2, 354 (90%) (MH+ + CH$_3$CN); 311.2, 313 (20%) (MH+) |

Biological Data for Representative Compounds of this Invention:

| Example | FP β-ER K$_i$ (nM) | FP α-ER K$_i$ (nM) | FP Selectivity | ERE β-ER EC$_{50}$ (nM) | ERE β-ER Max | ERE α-ER EC$_{50}$ (nM) | ERE α-ER Max | ERE Selectivity |
|---------|---------|---------|---------|---------|---------|---------|---------|---------|
| 1 | 1.7 | 18 | 10 | 1.2 | 98 | 61 | 103 | 52 |
| 3 | 4.8 | 121 | 25 | 23 | 89 | 497 | 102 | 22 |
| 5 | 290 | 1000 | 3 | 1000 | 98 | 1000 | 102 | 1.8 |
| 7 | 5.8 | 82 | 14 | 1.4 | 95 | 25 | 116 | 18 |

-continued

| Example | FP β-ER $K_i$ (nM) | FP α-ER $K_i$ (nM) | FP Selectivity | ERE β-ER $EC_{50}$ (nM) | ERE β-ER Max | ERE α-ER $EC_{50}$ (nM) | ERE α-ER Max | ERE Selectivity |
|---|---|---|---|---|---|---|---|---|
| 8 | 148 | 477 | 3 | | | | | |
| 10 | 0.38 | 5.6 | 15 | 0.017 | 103 | 6.0 | 109 | 363 |
| 12 | 1.8 | 54 | 30 | 0.5 | 81 | 76 | 37 | 153 |
| 22 | 1.2 | 14 | 12 | 0.616 | 98 | 6.4 | 83 | 10 |
| 23 | 646 | 2200 | 3 | 298 | 86 | 1000 | 78 | 14 |

Chemical Syntheses

The HPLC conditions used are the following unless stated otherwise: HPLC 2.1×50 mm $C_8$ 5 µm Zorbax Stablebond column; flow rate 1.4 mL/min, linear gradient from 15% B to 90% B over 4.0 min; A=water, 0.05% TFA; B=90% acetonitrile, 10% water, 0.05% TFA, UV detection at 254 nm or DAD and positive ionization mass spectrometry detection.

TFA: trifluoroacetic acid
DMSO: dimethylsulfoxide
DEAD: diethyl axodicarboxylate
$PPh_3$: triphenylphosphine
EDTA: ethylenediaminetetraacetic acid
$BBr_3$: boron tribromide Example 1

4-Chloro-6-hydroxy-2-(4-hydroxyphenyl)benzoxazole

1) Synthetic Method A: Synthesis of 2-amino-3-chloro-5-methoxyphenol

A solution of 3-chloro-5-methoxy-2-nitrophenol [1] (450 mg) and tin(II) chloride dihydrate (2 g, 4 eq.) in ethyl acetate (30 mL) was heated under reflux for 4 h. The mixture was cooled, diluted with ethyl acetate and aqueous potassium fluoride. The mixture was filtered through celite. The organic layer was washed with brine and dried over $MgSO_4$. Evaporation of the solvent afforded the title compound (280 mg) as a pale solid. NMR (DMSO-$d_6$): 9.74 (m, 1H), 6.33 (d, 1H, J=2.4 Hz), 6.30 (d, 1H, J=2.4 Hz), 4.19 (m, 2H), 3.60 (s, 3H).

Reference 1: Hodgson, Wignall, *J. Chem. Soc.*, 1928, 330. Prepared from 1-chloro-3,5-dimethoxybenzene by nitration with concentrated nitric acid in acetic anhydride below 10° C. to give 1-chloro-3,5-dimethoxy-2-nitrobenzene, and subsequent reaction with boron tribromide (1 eq.) in dichloromethane from −78° C. to 0° C.

2) Synthetic Method B: Synthesis of 4-chloro-2-(4-hydroxyphenyl)-6-methoxybenzoxazole Example 2

A solution of 2-amino-3-chloro-5-methoxyphenol (270 mg) and ethyl 4-hydroxybenzimidate hydrochloride (376 mg, 1.2 eq.) in absolute ethanol (5 mL) was heated under reflux for 4 h. The mixture was cooled, partitioned between ethyl acetate and water. The organic layer was dried over $MgSO_4$. After evaporation of the solvent, the residue was triturated with methanol to give the title compound (130 mg) as a light orange solid. NMR (DMSO-$d_6$): 10.35 (s, 1H), 8.00 (d, 2H, J=8.7 Hz), 7.39 (d, 1H, J=2.1 Hz), 7.10 (d, 1H, J=2.1 Hz), 6.96 (d, 2H, J=8.7 Hz), 3.85 (s, 3H); MS: 276 (MH$^+$).

3) Synthetic Method C: Synthesis of 4-chloro-6-hydroxy-2-(4-hydroxyphenyl)benzoxazole To a suspension of 4-chloro-2-(4-hydroxyphenyl)-6-methoxybenzoxazole (240 mg) in dichloromethane (5 mL) cooled at −78° C. was added boron tribromide (5 mL, 1M solution in dichloromethane, 5.7 eq.). The mixture was stirred at −78° C. for 10 min, warmed to room temperature and stirred for 3 h. The mixture was poured onto ice/water and extracted with ethyl acetate. The organic layer was washed with brine and dried over $MgSO_4$. Chromatography on a silica gel column (eluant: acetone-dichloromethane, gradient from 0:100 to 5:95) and trituration of the resulting solid in dichloromethane afforded the title compound (53 mg) as a solid. NMR (DMSO-$d_6$): 10.31 (s, 1H), 10.17 (s, 1H), 7.98 (d, 2H, J=8.4 Hz), 7.06 (s, 1H), 6.95 (d, 2H, J=8.4 Hz), 6.87 (s, 1H); MS: 262 (MH$^+$); HPLC $t_R$: 1.99 min.

Example 3

6-Hydroxy-2-(4-hydroxyphenyl)-4-methylbenzoxazole

1) Synthesis of 2-(4-hydroxyphenyl)-6-methoxy-4-methylbenzoxazole (Example 4) According to synthetic method B, from 2-amino-5-methoxy-3-methylphenol [2] (440 mg) was obtained the title compound (340 mg) as a light orange solid. MS: 256 (MH$^+$).

Reference 2: Musso H; Beecken H, *Chem. Ber.* 1961, 94, 585; made from 3,5-dimethoxytoluene by nitration and monodeprotection of the 3-methoxy with $BBr_3$ similarly to Ref. 1 followed by reduction of the nitro group to the amino by hydrogenation with palladium on charcoal.

2) According to synthetic method C, the above compound (220 mg) was converted to 6-hydroxy-2-(4-hydroxyphenyl)-4-methylbenzoxazole (112 mg) as a light pinkish powder. NMR (DMSO-$d_6$): 10.14 (s, 1H), 9.58 (s, 1H), 7.94 (d, 2H, J=8.7 Hz), 6.92 (d, 2H, J=8.7 Hz), 6.84 (s, 1H), 6.63 (s, 1H), 2.46 (s, 3H); MS: 242 (MH$^+$).

Example 5

4,6-Dihydroxy-2-(4-hydroxyphenyl)benzoxazole

A mixture of 1-nitro-2,4,6-trihydroxybenzene (1 g) and 10% palladium on charcoal (200 mg) in absolute ethanol (10 mL) was stirred for 18 h at room temperature under a 50-PSI atmosphere of hydrogen. The solids were filtered rapidly. To the resulting filtrate was added ethyl 4-hydroxybenzimidate hydrochloride (1.17 g). The mixture was heated at reflux for 5 h under nitrogen, cooled and partitioned between ethyl acetate and water. The organic layer was washed with water and brine, and dried over MgSO4. Chromatography on silica gel (eluant: acetone-dichloromethane, gradient 10:90 to 20:80) and trituration of the resulting solid with ether afforded the title compound (28 mg) as a light pinkish solid. NMR (DMSO-$d_6$): 10.15 (m, 2H), 9.53 (s, 1H), 7.91 (d, 2H, J=8.7 Hz), 6.92 (d, 2H, J=8.7 Hz), 6.48 (d, 1H, J=1.5 Hz), 6.26 (d, 1H, J=1.5 Hz); MS: 244 (MH$^+$).

Example 6

6-Hydroxy-2-(4-hydroxyphenyl)benzoxazole

According to synthetic method B except that pyridine (300 μL) was added, from 4-aminoresorcinol hydrochloride (435 mg) and ethyl 4-hydroxybenzimidate hydrochloride was obtained the title compound (432 mg) as an off-white solid. The work-up of the reaction was modified as follows: After completion of the reaction, the mixture was diluted with ether and water, and filtered. The solids were washed with water and ether, and dried under high vacuum. NMR (DMSO-$d_6$): 10.23 (s br, 1H), 9.76 (s br, 1H), 7.95 (d, 2H, J=8.4 Hz), 7.50 (d, 1H, J=8.4 Hz), 7.05 (d, 1H, J=1.8 Hz), 6.94 (d, 2H, J=8.4 Hz), 6.81 (dd, 1H, J=8.4 Hz, J'=1.8 Hz); MS: 228 (MH$^+$).

Example 7

5-Hydroxy-2-(4-hydroxyphenyl)benzoxazole

According to synthetic method B, from 2-amino-4-methoxyphenol [3] (500 mg) and ethyl 4-hydroxybenzimidate hydrochloride was obtained 2-(4-hydroxyphenyl)-5-methoxybenzoxazole (676 mg; Example 8). NMR (DMSO-$d_6$): 10.28 (s, 1H), 8.01 (d, 2H, J=8.7 Hz), 7.61 (d, 1H, J=9 Hz), 7.28 (d, 1H, J=2.4 Hz), 6.94 (m, 3H), 3.82 (s, 3H); MS: 242 (MH$^+$). This compound. (452 mg) was converted to the title compound (121 mg) according to synthetic method C. NMR (DMSO-$d_6$): 10.24 (s, 1H), 9.42 (s br, 1H), 7.99 (d, 2H, J=8.7 Hz), 7.49 (d, 1H, J=9 Hz), 7.02 (d, 1H, J=2.1 Hz), 6.94 (d, 2H, J=8.7 Hz), 6.78 (dd, 1H, J=9 Hz, J'=2.1 Hz); MS: 226 (M–H).

Reference 3: Lok R, Leone R E, Williams A J, *J. Org. Chem.* 1996, 61, 3289.

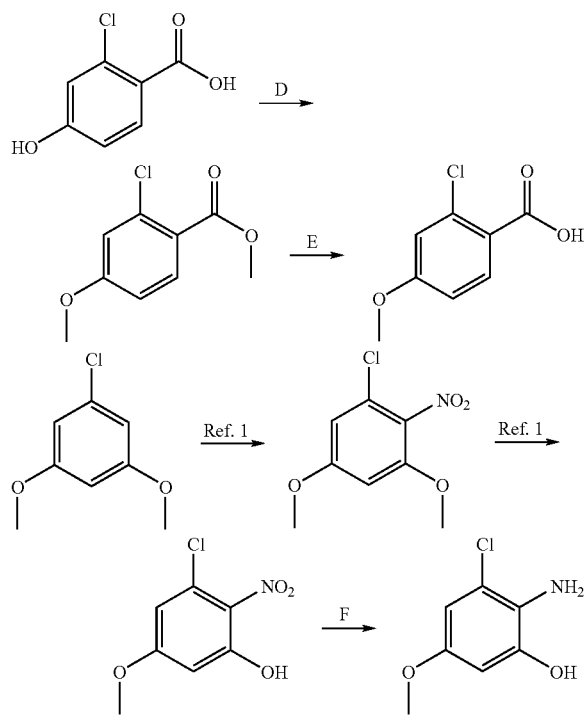

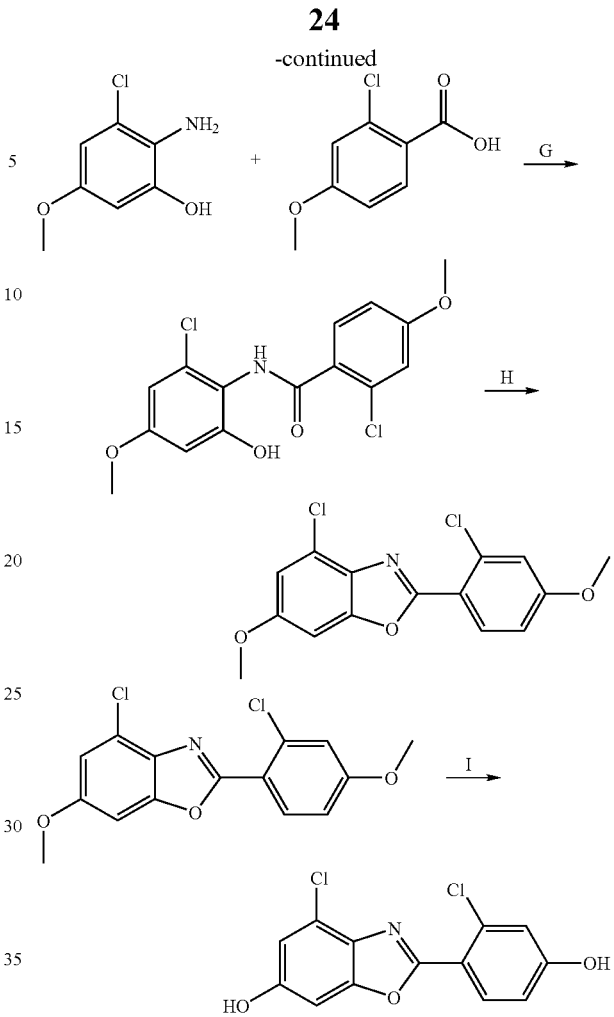

Example 9

4-Chloro-2-(2-chloro-4-hydroxy-phenyl)-benzooxazol-6-ol

Synthetic Method D: Synthesis of 2-chloro-4-methoxy-benzoic acid methyl ester

To 2-chloro-4-hydroxy-benzoic acid hydrate (1.1 g) in DMF (20 mL) was added $K_2CO_3$ (2.4 g) and methyl iodide (0.75 mL). After 2 h, water was added to the reaction mixture and extracted with ethyl acetate. The organic layer was washed with brine (3×) and dried over $MgSO_4$. Flash chromatography on silica gel eluting with 10% ethyl acetate-hexane afforded 1.13 g (95%) of the title compound as an oil. MS: 201 (MH$^+$), HPLC $t_R$: 2.52 min.

Synthetic Method E: Synthesis of 2-chloro-4-methoxy-benzoic acid

To 2-chloro-4-methoxy-benzoic acid methyl ester (1.1 g) in THF/MeOH/water (12 mL/3 mL/3 mL) at room temperature was added LiOH (461 mg) dissolved in water. After 2 h, the reaction mixture was adjusted to pH 4 with 1N HCl and partitioned between ethyl acetate and water. The organic layer was washed with brine and dried over $MgSO_4$. Trituration of the resulting solid in ether afforded 1.0 g (98%) of the title compound. MS: 187 (MH$^+$), HPLC $t_R$: 2.04 min.

Synthetic Method F: Synthesis of 2-amino-3-chloro-5-methoxyphenol

To 3-chloro-5-methoxy-2-nitrophenol, synthetic method A[1], (200 mg) in 95% EtOH (10 mL) was added 5% Ru/C (20 mg) and hydrazine (0.36 mL). The mixture was placed in an oil bath and heated to 85° C. for 2 h. After reaction cooled, the mixture was diluted with ethyl acetate and filtered through a pad of celite and concentrated. Flash chromatography on silica gel eluting with 30% ethyl acetate-hexane afforded 138 mg (76%) of the title compound as a solid. MS: 174 (MH$^+$), HPLC $t_R$: 0.84 min.

Synthetic Method G: Synthesis of 2-chloro-N-(2-chloro-6-hydroxy-4-methoxy-phenyl)-4-methoxy-benzamide.

To 2-chloro-4-methoxy-benzoic acid (100 mg) in CH$_2$Cl$_2$ (5 mL) was added oxalyl chloride (0.05 mL) and 2 drops of DMF. The reaction mixture was allowed to stir for 2 h and then concentrated to dryness. The resulting acid chloride was taken up in CH$_2$Cl$_2$ and added drop wise to a coot mixture of 2-amino-3-chloro-5-methoxyphenol (94 mg), 10% Na$_2$CO$_3$ (2.5 mL), and CH$_2$Cl$_2$ (5 mL) placed in an ice water bath. After 2 h, water was added to the reaction and extracted with additional CH$_2$Cl$_2$ and the organic layer was dried over Na$_2$SO$_4$. Flash chromatography on silica gel eluting with 0% to 30% ethyl acetate-hexane afforded 100 mg (54%) of the title compound as an solid. MS: 342 (MH$^+$), HPLC $t_R$: 2.54 min.

Synthetic Method H: Synthesis of 4-chloro-2-(2-chloro-4-methoxy-phenyl)-6-methoxy-benzooxazole Reference 4. Wang, F.; Hauske, J. R.; *Tetrahedron Lett.* 1997, 38 (37) 6529–6532

2-Chloro-N-(2-chloro-6-hydroxy-4-methoxy-phenyl)-4-methoxy-benzamide (40 mg) was completely dissolved in THF (5 mL) and PPH$_3$ (46 mg) was added and the mixture was stirred until all PPH$_3$ dissolved. To this mixture was added drop wise DEAD (0.03 mL) diluted in THF (0.5 mL). The mixture was stirred at room temperature for 2 h and the reaction mixture was diluted with ethyl acetate and washed with water, brine, dried over MgSO$_4$ and concentrated. Flash chromatography on silica gel eluting with 10% to 30% ethyl acetate-hexane afforded 32 mg (85%) of the title compound as a solid. MS: 324 (MH$^+$), HPLC $t_R$: 3.18 min.

Synthetic Method I: Synthesis of 4-chloro-2-(2-chloro-4-hydroxy-phenyl)-benzooxazol-6-ol To 4-chloro-2-(2-chloro-4-methoxy-phenyl)-6-methoxybenzooxazole (52 mg) in CH$_2$Cl$_2$ (2 mL) placed in and ice water bath was added drop wise 1.0 M BBr$_3$ in CH$_2$Cl$_2$ (0.96 mL, 6 eq). After the reaction stirred over night, the mixture was placed in an ice water bath and excess MeOH was added drop wise to quench excess BBr$_3$ and the mixture was stirred for an additional 20 min and concentrated. Flash chromatography on silica gel eluting with 0% to 40% ethyl acetate-hexane afforded 35 mg (74%) of the title compound as a solid. MS: 296 (MH$^+$), HPLC $t_R$: 2.32 min.

Example 10

7-Bromo-2-(4-hydroxy-phenyl)-benzooxazol-5-ol

Synthetic Method J: Synthesis of 2-bromo-4-methoxy-6-nitro-phenol

4-Methoxy-2-nitro-phenol (10 g) was dissolved in glacial acetic acid (60 mL) and CH$_3$CO$_2$Na (8.2 g) was added. Next, bromine (3 mL) dissolved in glacial acetic acid (12 mL) was added drop wise to the stirring solution at room temperature. After complete addition of bromine, the mixture was stirred for 30 min at room temperature and then placed in an oil bath at 75° C. for 2 h. After reaction mixture cooled to room temperature, concentrated HCl (500 mL) was slowly added to the mixture followed by addition of ethyl acetate (500 mL). The layers were separated and the organic layer was washed with water, brine, dried (Na$_2$SO$_4$). Flash chromatography on silica gel eluting with 5% ethyl acetate-hexane afforded 8.8 g (60%) of the title compound as a solid. MS: 218 (MH$^+$–30), HPLC $t_R$: 2.40 min.

According to synthetic methods F, G, H (except the reaction mixture was heated in an oil bath at 85° C. for 2 h), and I was obtained 7-bromo-2-(4-hydroxy-phenyl)-benzooxazol-5-ol. MS: 308 (MH$^+$), HPLC $t_R$: 2.29 min. NMR (DMSO-d$_6$): 10.34 (s, 1H), 9.82 (s, 1H), 7.99 (d, 2H, J=8.4 Hz), 6.95–7.04 (m, 4H).

Example 12

7-Bromo-2-(3-chloro-4-hydroxy-phenyl)-benzooxazol-5-ol

According to synthetic methods J (using 4-methoxy-2-nitro-phenol), F, G (using 3-chloro-4-methoxy-benzoic acid), H (except the reaction mixture was heated in an oil bath at 85° C. for 2 h), and I the title compound was obtained. MS: 341 (MH$^+$), HPLC $t_R$: 2.30 min. NMR (DMSO-d$_6$): 11.17 (s, 1H), 9.85 (s, 1H), 8.04 (s, 1H), 7.95 (d, 1H, J=8.2 Hz), 7.18 (d, 1H, J=8.3 Hz), 7.05 (s, 1H), 7.02 (s, 1H).

Example 13

2-(4-Hydroxy-phenyl)-7-iodo-benzooxazol-5-ol

Synthetic Method K: Synthesis of 7-iodo-5-methoxy-2-(4-methoxy-phenyl)-benzooxazole To 7-bromo-5-methoxy-2-(4-methoxy-phenyl)-benzooxazole (100 mg, from example 10, synthetic methods F, G, H, J), was added CuI (285 mg), KI (497 mg) and DMSO (5 mL). The mixture was placed in an oil bath and heated to 180° C. for 4 h. The mixture was cooled to room temperature and diluted with ethyl acetate and washed with brine (3×), dried (MgSO$_4$), and concentrated. The crude solid was taken up in ethyl acetate and filtered through a pad of celite and the filtrate was concentrated to dryness. Flash chromatography on silica gel eluting with 20% ethyl acetate-hexane afforded 80 mg (70%) of the title compound as a solid. MS: 382 (MH$^+$), HPLC $t_R$: 3.00 min.

According to synthetic method I was obtained 2-(4-Hydroxyphenyl)-7-iodo-benzooxazol-5-ol. MS: 354 (MH$^+$), HPLC $t_R$: 2.26 min.

Example 21

7-Chloro-2-(4-hydroxy-phenyl)-benzooxazol-5-ol

Synthetic Method L: Synthesis of 7-chloro-5-methoxy-2-(4-methoxy-phenyl)-benzooxazole To 7-iodo-5-methoxy-2-(4-methoxy-phenyl)-benzooxazole (150 mg) in DMF (6 mL) was added CuCl (195 mg). The mixture was placed in an oil bath and heated to 150° C. for 3 h. The mixture was cooled to room temperature and diluted with ethyl acetate and washed with 1N HCl, brine (3×), dried (MgSO$_4$), and concentrated. Flash chromatography on silica gel eluting with 20% ethyl acetate-hexane afforded 100 mg (88%) of the title compouud as a solid. MS: 290 (MH$^+$), HPLC $t_R$: 2.89 min.

According to synthetic method I was obtained 7-chloro-2-(4-hydroxy-phenyl)-benzooxazol-5-ol. MS: 262 (MH$^+$), HPLC $t_R$: 2.09 min.

Example 22

5-Hydroxy-2-(4-hydroxy-phenyl)-benzooxazole-7-carbonitrile

Synthetic Method M: Synthesis of 5-hydroxy-2-(4-hydroxy-phenyl)-benzooxazole-7-carbonitrile To 7-bromo-2-(4-hydroxy-phenyl)-benzooxazol-5-ol (96 mg) in DMF (3 mL) was added CuCN (84 mg). The mixture was placed in an oil bath and heated to 150° C. for 3 h. The mixture was cooled to room temperature and diluted with ethyl acetate and washed with 1N HCl, saturated aqueous EDTA, brine (3×), dried (Na$_2$SO$_4$), and concentrated. Flash chromatography on silica gel eluting with 20% ethyl acetate-hexane afforded 20 mg (25%) of the title compound as a solid. MS: 253 (MH$^+$), HPLC t$_R$: 2.06 min.

Example 23

5-Hydroxy-2-(4-hydroxy-phenyl)-benzooxazole-7-carboxylic acid amide

Synthetic Method N: Synthesis of 5-methoxy-2-(4-methoxy-phenyl)-benzooxazole-7-carbonitrile To 7-bromo-5-methoxy-2-(4-methoxy-phenyl)-benzooxazole (200 mg) in DMF (5 mL) was added CuCN (80 mg). The mixture was placed in an oil bath and heated to 150° C. for 3 h. The mixture was cooled to room temperature and diluted with ethyl acetate and washed with 1N HCl, brine (3×), dried (Na$_2$SO$_4$), and concentrated. Flash chromatography on silica gel eluting with 20% ethyl acetate-hexane afforded 85 mg (50%) of the title compound as a solid. MS: 281 (MH$^+$), HPLC t$_R$: 2.71 min.

According to synthetic method I was obtained 5-hydroxy-2-(4-hydroxy-phenyl)-benzooxazole-7-carboxylic acid amide by residual acid hydrolysis of the nitrile substituent upon concentration of the crude reaction mixture. MS: 271 (MH$^+$); HPLC t$_R$: 2.04 min.

Example 30

2-(2-Cyano-4-hydroxy-phenyl)-5-hydroxy-benzooxazole-7-carbonitrile

Synthetic Method O: Synthesis of 2-(2-cyano-4-hydroxy-phenyl)-5-hydroxy-benzooxazole-7-carbonitrile To 2-(2-chloro-4-hydroxy-phenyl)-7-iodo-benzooxazol-5-ol (279 mg) in DMF (5 mL) was added CuCN (97 mg). The mixture was placed in an oil bath and heated to 150° C. for 3 h. The mixture was cooled to room temperature and diluted with ethyl acetate and washed with 1N HCl, saturated aqueous EDTA, brine (3×), dried (Na$_2$SO$_4$), and concentrated. Material was purified by preparative LC/MS. MS: 278 (MH$^+$), HPLC t$_R$: 1.92 min. The HPLC conditions used are the following: HPLC Waters Corp. Novapak HR™ C 18 RCM 40×100 mm 6 µm particle; flow rate 40 mL/min, linear gradient from 35% B to 65% B over 15 min; A=water, 0.1% TFA; B=MeOH, UV detection at 254 nm and positive ionization mass spectrometry detection Example 31

6-Bromo-2-(4-hydroxy-phenyl)-benzooxazol-5-ol

Synthetic Method P: Synthesis of 1-bromo-2,5-dimethoxy-4-nitro-benzene

The title compound was synthesized according to the methods describe by Reference 5: Jean-Luc Grenier, Jean-Pierre Catteau and Philippe Cotelle, *Synthetic Communications*, 29(7), 1201–1208 (1999).

According to synthetic methods F, G, H and I, was obtained 6-bromo-2-(4-hydroxy-phenyl)-benzooxazol-5-ol. MS: 308 (MH$^+$), HPLC t$_R$: 2.18 min.

Example 32

4-(6-Hydroxy-benzooxazol-2-yl)-thiazolidin-2-one

Reference 6. Steven W. Goldstien and Paul J. Dambek, *J. Heterocyclic Chem*. 1990, 27, 225.

Synthetic Method Q: Synthesis of 2-oxo-thiazolidine-4-carboxylic acid (2-hydroxy-4-methoxy-phenyl)-amide To 2-oxo-thiazolidine-4-carboxylic acid (492 mg) in CH$_2$Cl$_2$ (10 mL) was added oxalyl chloride (0.35 mL) and 2 drops of DMF. The reaction mixture was allowed to stir for 2 h and then concentrated to dryness. The resulting acid chloride was taken up in CH$_2$Cl$_2$ and added drop wise to a cool mixture of 2-amino-5-methoxy-phenol (490 mg), Et$_3$N (1.56 mL), and CH$_2$Cl$_2$ (10 mL) placed in an ice water bath. After 2 h, water and CH$_2$Cl$_2$ was added to the reaction mixture and layers separated. The organic layer was washed with 1N HCl. To the HCl aqueous layer was added brine and CH$_2$Cl$_2$ to salt-out the title compound, the organic layers were combined, dried (Na$_2$SO$_4$) and concentrated to afford 448 mg (60%) of the title compound. The crude amide was used directly in the next step. MS: 269 (MH$^+$), HPLC t$_R$: 1.37 min.

Synthetic Method R: Synthesis of 4-(6-methoxy-benzooxazol-2-yl)-thiazolidin-2-one To 2-oxo-thiazolidine-4-carboxylic acid (2-hydroxy-4-methoxy-phenyl)-amide (50 mg) in p-xylene (3 mL) was added pyridinium p-toluenesolfonate (42 mg). The reaction mixture was refluxed for 2 h and then allowed to cool to room temperature. The mixture was diluted with ethyl acetate and water was added. The layers were separated and the organic layer was washed with brine, dried (Na$_2$SO$_4$), and concentrated. Flash chromatography on silica gel eluting with 3% methanol-methylene chloride afforded 42 mg (90%) of the title compound as a solid. MS: 251 (MH$^+$) HPLC t$_R$: 1.60 min.

According to synthetic method I was obtained 4-(6-hydroxy-benzooxazol-2-yl)-thiazolidin-2-one 30 mg (63%). MS: 237 (MH$^+$) HPLC t$_R$: 1.20 min.

Example 33

7-Bromo-2-phenyl-benzooxazol-5-ol tert-Butyl-chloro-silane (0.25 ml) was added to a mixture of 2-bromo-4-methoxy-6-nitro-phenol (0.124 g), chromium (II) chloride (0.012 g) and manganese (0) powder (0.137 g) in dimethylformamide (3 mL). The mixture was subjected to microwaves for 4 min at 150° C. Benzaldehyde (0.06 mL) was added and the reaction was subjected to microwaves for 6 min at 150° C. Water (0.5 mL) was added, then after 30 min the mixture was filtered through a pad of celite. The above procedure was repeated three more times. The combined filtrate was partitioned between dilute aq. HCl (100 mL) and ethyl acetate (100 mL). The organic layer was dried over sodium sulfate, filtered through celite and concentrated. Chromatography on silica gel (eluant: gradient 0 to 30% ethyl acetate:hexane) afforded 7-bromo-5-methoxy-2-phenyl-benzooxazole (0.13 g). MS: 304 (95%), 306.4 (100%) (MH$^+$); HPLC t$_R$: 2.79 min.

Reference 7: *J. Org. Chem*. 2001, 66, 991–996. 7-Bromo-5-methoxy-2-phenyl-benzooxazole was deprotected using synthetic method C to give the title compound (0.060 g) after purification on silica gel (eluant: 5 to 30% ethyl acetate:hexane). MS: 290.3, 292.3 (MH$^+$); HPLC t$_R$: 2.44 min.

Example 35

2-(1H-Indazol-5-yl)-benzooxazol-6-ol

1H-Indazole-5-carbonitrile hydrochloride (1.5 g) was suspended in ethanol (15 mL) at 0° C. The mixture was saturated with hydrogen chloride while the temperature was raised to room temperature. The reaction was then left overnight. Diethylether was added and the resulting precipitate, 1H-indazole-5-carboximidic acid ethyl ester.2HCl (1.39 g), was collected and dried in under high vacuum. According to synthetic method B except that pyridine (540 ?L) was added, from 4-amino-benzene-1,3-diol hydrochloride (0.36 mg) and 1H-indazole-5-carboximidic acid ethyl ester hydrochloride (0.71 g) was obtained the title compound (0.34 mg) as an off-white solid. The work-up of the reaction was modified as follows: After completion of the reaction, the mixture was diluted with ether and water, and filtered. The solids were washed with water and ether, and dried under high vacuum. MS: 252.4 (MH$^+$); HPLC $t_R$: 1.80 min.

Example 36

5-(7-Bromo-5-methoxy-benzooxazol-2-yl)-pyrrolidin-2-one

2-Amino-6-bromo-4-methoxy-phenol (0.40 g), 1,3-dimethylaminopropyl)-3-ethylcarbodiimide (1.06 g), 1-hydroxybenzotriazole (0.50 g), dimethylaminopyridine (0.22 g) and DL-5-oxo-pyrrolidine-2-carboxylic acid (0.25 g) were reacted together in methylene chloride (7.3 mL). After 3 h, the reaction was diluted with methylene chloride (10 mL) and washed successively with 1N HCl (10 mL), sat. aq. NaHCO$_3$ (10 mL), sat. aq. NaCl (10 mL). The organic layer was dried over sodium sulfate, filtered through celite and concentrated. Chromatography on silica gel (eluant: 0 to 20% methanol:methylene chloride) afforded 5-oxo-pyrrolidine-2-carboxylic acid (3-bromo-2-hydroxy-5-methoxy-phenyl)-amide (0.18 g). MS: 370.2 (100%), 372.2 (90%) (MH$^+$); HPLC $t_R$: 1.51 min. 5-Oxo-pyrrolidine-2-carboxylic acid (3-bromo-2-hydroxy-5-methoxy-phenyl)-amide was cyclized according to synthetic method R to obtain the title compound (0.09 g) after purification on silica gel (eluant: 0 to 30% methanol:methylene chloride). MS: 352.2 (100%), 354.2 (95%) (MH$^+$+CH$_3$CN), 311.2 (20%), 313.2 (20%) (MH$^+$).; HPLC $t_R$: 1.84 min.

Reference Example 37

5-Methoxy-2-aminobenzenethiol Hydrochloride

Prepared following literature procedure: Can. J. Chem. 43, 1965, 2610.

Example 38

6-Hydroxy-2-R-benzothiazol

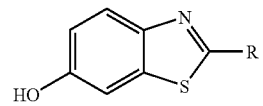

5-Methoxy-2-aminobenzenethiol hydrochloride was dissolved in 1-methyl-2-pyrrolidinone. After triethylamine (1 eq) was added, the mixture was stirred at room temperature for 10 min. Acid chloride (1 eq) was then added and the mixture was heated at 100° C. for 1 h. The mixture was then cooled to room temperature and 1N NaOH was added to PH 9. The solid was collected by filtration and washed with water. The solid was further dried on vacuum to give 6-methoxy-2-R-benzothiazol (yield step 1) which was treated with boron tribromide under standard procedure to give 6-hydroxy-2-R-benzothiazol (yield step 2).

| R group |  |  |  |  |
|---|---|---|---|---|
| yield on step 1 | 68 | 29 | 70 | 85 |
| yield on step 2 | 66 | 68 | 39 | 85 |
| Mass Spec MH$^+$ | 234 | 218 | 253 | 297 |

Example 39

4-Methyl-6-methoxy-2-(4-methoxy-phenyl)-benzothiazole

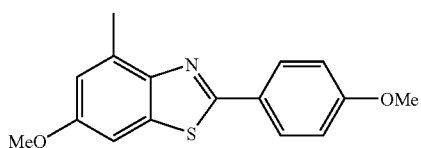

To a solution of 4-bromo-6-methoxy-2-(4-methoxy-phenyl)-benzothiazole (1.0 g, 2.86 mmol) in dry toluene (25 mL) was added potassium carbonate (4.2 g, 30.4 mmol), methylboronic acid (0.92 g, 15.3 mmol) and tetrakis(triphenylphosphine)palladium (0.44 g, 0.38 mmol). The mixture was heated to 100° C. for 24 h, then cooled to room temperature. The mixture was diluted with ethylacetate and washed with water, saturated sodium carbonate and brine. After chromatographic purification gave 4-methyl-6-methoxy-2-(4-methoxy-phenyl)-benzothiazole as a white solid (0.63 g, 77% yield). Mass spec: MH$^+$=286.

Example 40

4-Methyl-6-hydroxy-2-(4-hydroxy-phenyl)-benzothiazole

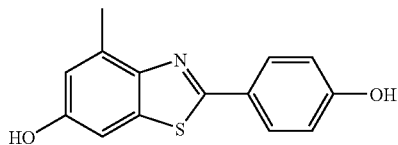

4-Methyl-6-methoxy-2-(4-methoxy-phenyl)-benzothiazole (174 mg, 0.61 mmol) was treated with boron tribromide under standard condition to give 4-methyl-6-hydroxy-2-(4-hydroxy-phenyl)-benzothiazole (105 mg, 67% yield) as a yellow solid. Mass spec: $MH^+=258$.

Example 41

4-Bromomethyl-6-methoxy-2-(4-methoxy-phenyl)-benzothiazole

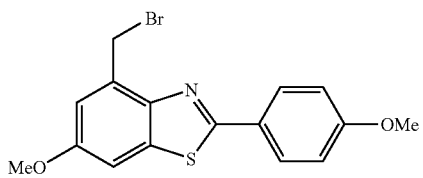

4-Methyl-6-methoxy-2-(4-methoxy-phenyl)-benzothiazole (0.53 g, 1.87 mmol), N-bromosuccinimide (0.33 g, 1.87 mmol) and benzoyl peroxide (9 mg) were suspended in carbon tetrachloride (6 mL) and refluxed for 3.5 h, then cooled to room temperature. Solvent was evaporated and the mixture was purified by chromatography to give 4-bromomethyl-6-methoxy-2-(4-methoxy-phenyl)-benzothiazole (0.47 g, 70% yield) as a white solid. Mass spec: $MH^+=364$.

Example 42

4-Cyanomethyl-6-methoxy-2-(4-methoxy-phenyl)-benzothiazole

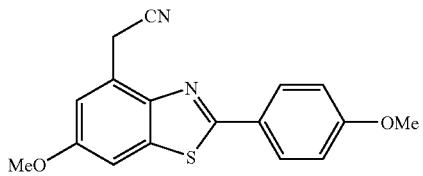

To a solution of 4-bromomethyl-6-methoxy-2-(4-methoxy-phenyl)-benzothiazole (0.47 g, 1.29 mmol) in ethanol (6 mL) was added a solution of potassium cyanide (0.1 g, 1.54 mmol) in water (0.5 mL). The mixture was refluxed for 1.5 h, then cooled to room temperature. Ethanol was evaporated and the mixture was extracted with ethylacetate. After chromatographic purification gave 4-cyanomethyl-6-methoxy-2-(4-methoxy-phenyl)-benzothiazole as a yellow solid (0.29 g, 73% yield). Mass spec: $MH^+=311$.

Example 43

4-Cyanomethyl-6-hydroxy-2-(4-hydroxy-phenyl)-benzothiazole

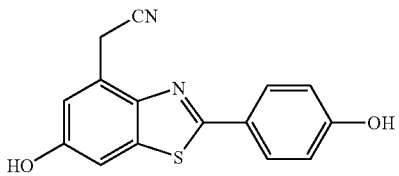

4-Methylcyano-6-methoxy-2-(4-methoxy-phenyl)-benzothiazole (0.29 g, 0.94 mmol) was treated with boron tribromide under standard condition to give 4-cyanomethyl-6-hydroxy-2-(4-hydroxy-phenyl)-benzothiazole (116 mg, 44% yield) as a yellow solid. Mass spec: $MH^+=283$.

Example 44

4-Trimethylsilylacetylene-6-methoxy-2-(4-methoxy-phenyl)-benzothiazole

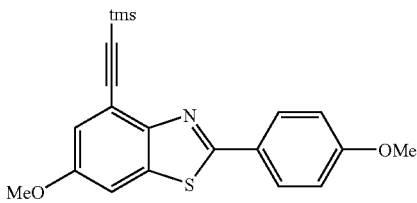

4-Bromo-6-methoxy-2-(4-methoxy-phenyl)-benzothiazole (0.3 g, 0.857 mmol), (trimethylsilyl)acetylene (0.48 mL, 3.43 mmol), triethylamine (0.48 mL, 3.43 mmol) and tetrakis(triphenylphosphine)palladium (0.2 g, 0.171 mmol) were suspended in THF (6 mL) in a sealed tube and heated to 70° C. for 24 h, then cooled to room temperature. Ethylacetate and water were added, the ethylacetate layer was washed with brine. After chromatigraphic purification gave 4-trimethylsilylacetylene-6-methoxy-2-(4-methoxy-phenyl)-benzothiazole (0.132 g, 42% yield) as a yellow solid. Mass spec: $MH^+=368$.

Example 45

4-Acetylene-6-methoxy-2-(4-methoxy-phenyl)-benzothiazole

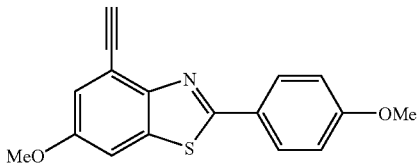

To a solution of 4-trimethylsilylacetylene-6-methoxy-2-(4-methoxy-phenyl)-benzothiazole (0.216 g, 0.588 mmol) in THF (5 mL) was added 1N sodium hydroxide (1.18 mL, 1.18 mmol) and the solution was stirred at room temperature for 3 h. THF was then evaporated. Water and ethylacetate were added. Combined ethylacetate were concentrated. After chromatigraphic purification gave 4-acetylene-6-methoxy-2-(4-methoxy-phenyl)-benzothiazole (0.113 g, 65% yield) as a yellow solid. Mass spec: $MH^+=296$

Example 46

4-Acetylene-6-hydroxy-2(4-hydroxy-phenyl)-benzothiazole

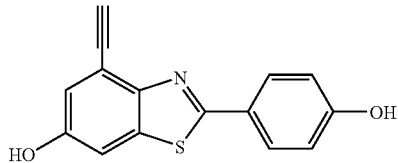

4-Acetylene-6-methoxy-2-(4-methoxy-phenyl)-benzothiazole (93 mg, 0.315 mmol) was treated with boron tribromide under standard condition to give 4-acetylene-6-hydroxy-2-(4-hydroxy-phenyl)-benzothiazole (47 mg, 46% yield) as a yellow solid. Mass spec: $MH^+=268$

Example 47

4-Methylcarboxy-6-methoxy-2-(4-methoxy-phenyl)-benzothiazole

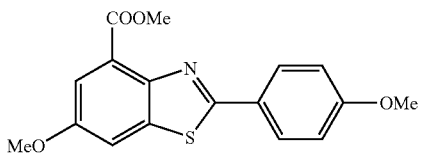

4-Bromo-6-methoxy-2-(4-methoxy-phenyl)-benzothiazole (1.0 g, 2.86 mmol), triethylamine (0.96 mL, 7.15 mmol) palladium acetate (31 mg, 0.143 mmol) and 1,3-bis(diphenylphosphino)propane (57 mg, 0.143 mmol) were suspended in methanol (7 mL) and DMSO (7 mL). The mixture was heated to 75° C. and bubbled with CO for 20 min. The mixture was then heated under CO for 48 h. After cooling to room temperature, brine was added. The mixture was extracted with ethylacetate. Combined ethylacetate were concentrated. After chromatographic purification gave 4-methylcarboxy-6-methoxy-2-(4-methoxy-phenyl)-benzothiazole (0.37 g, 39% yield) as a white solid. Mass spec: $MH^+=330$.

Example 48

4-Carboxy-6-methoxy-2-(4-methoxy-phenyl)-benzothiazole

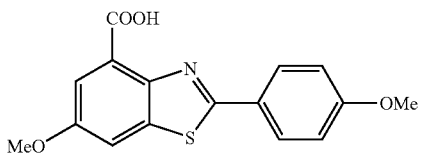

To a solution of 4-methylcarboxy-6-methoxy-2-(4-methoxy-phenyl)-benzothiazole (0.37 g, 1.12 mmol) in THF (6 mL) and water (3 mL) was added 1N sodium hydroxide (2.24 mL, 2.24 mmol) and the solution was stirred at room temperature for 24 h. THF was then evaporated. 1 N HCl was added to PH 1. The solid was collected by filtration and washed with water to give 4-carboxy-6-methoxy-2-(4-methoxy-phenyl)benzothiazole (0.29 g, 82% yield) as a white solid. Mass spec: $MH^+=316$.

Example 49

4-Carboxy-6-hydroxy-2-(4-hydroxy-phenyl)-benzothiazole

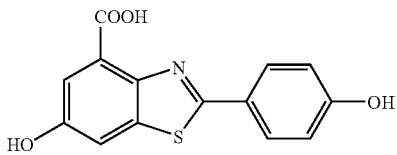

4-Carboxy-6-methoxy-2-(4-methoxy-phenyl)-benzothiazole (50 mg, 0.159 mmol) was treated with boron tribromide under standard condition to give 4-carboxy-6-hydroxy-2-(4-hydroxy-phenyl)-benzothiazole (34 mg, 74% yield) as a yellow solid. Mass spec: $MH^+=288$. $^1H$ NMR (DMSO-$d_6$): 10.24 (s, 1H), 10.16 (s, 1H), 7.91 (d, 2H), 7.67 (s, 1H), 7.48 (s, 1H), 6.95 (d, 2H).

Example 50

4-Carboxyamide-6-hydroxy-2-(4-hydroxy-phenyl)-benzothiazole

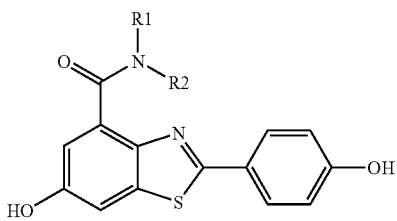

4-Carboxy-6-methoxy-2-(4-methoxy-phenyl)-benzothiazole (1 eq), 1-hydroxybenzotriazole (2.4 eq), dimethylamine or methylamine (3.7 eq) and 1-ethyl-3-(3-dimethylaminopropyl)carbodiimide hydrochloride (2.3 eq) were suspended in DMF and stirred at room temperature for 5 min. Triethylamine (4.1 eq) was added and the mixture was stirred at room temperature for 24 h. [when $R_1=R_2=H$, only 1-ethyl-3-(3-dimethylaminopropyl) carbodiimide hydrochloride (2.05 eq) and 1-hydroxybenzotriazole ammonia (2.46 eq) were added]. Saturated sodium bicarbonate was added and the mixture was extrated with ethylacetate. Combined ethylacetate were washed with brine, concentrated. After chromatographic purification gave the product (yield step 1) which was further treated with boron tribromide under standard condition to give 4-carboxyamide-6-hydroxy-2-(4-hydroxy-phenyl)-benzothiazole (yield step 2).

| $R_1/R_2$ | $R_1 = R_2 =$ Me | $R_1 =$ H, $R_2 =$ Me | $R_1 = R_2 =$ H |
|---|---|---|---|
| yield on step 1 | 86 | 67 | 91 |
| yield on step 2 | 100 | 70 | 44 |
| Mass Spec $MH^+$ | 315 | 301 | 287 |

Example 51

6-Methoxy-2-(2-bromo-3-methoxy-phenyl)-benzothiazole

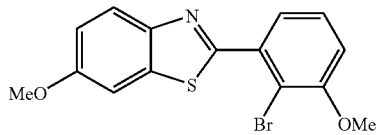

5-Methoxy-2-aminobenzenethiol hydrochloride (83 g, 4.33 mmol) was dissolved in 1-methyl-2-pyrrolidinone (10 mL). After triethylamine (0.60 mL, 4.33 mmol) was added, the mixture was stirred at room temperature for 10 min. 2-Bromo-3-methoxybenzoyl chloride (1.08 g, 4.33 mmol) in 1-methyl-2-pyrrolidinone (10 mL) was then added and the mixture was heated at 100° C. for 40 min. The mixture was cooled to room temperature and 1N NaOH was added to PH 9. The mixture was extracted with ethylacetate and combined ethylacetate were washed with brine, concentrated. After chromatographic purification gave 6-methoxy-2-(2-bromo-3-methoxy-phenyl)-benzothiazole (0.98 g, 65% yield) as a yellow solid. Mass spec: MH$^+$=350.

Example 52

6-Hydroxy-2-(2-bromo-3-hydroxy-phenyl)-benzothiazole

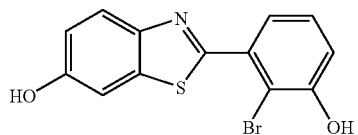

6-Methoxy-2-(2-bromo-3-methoxy-phenyl)-benzothiazole (0.144 g, 0.411 mmol) was treated with boron tribromide under standard condition to give 6-hydroxy-2-(2-bromo-3-hydroxy-phenyl)-benzothiazole (35 mg, 26% yield) as a yellow solid. Mass spec: MH$^+$=322.

Example 53

6-Methoxy-2-(2-methyl-3-methoxy-phenyl)-benzothiazole

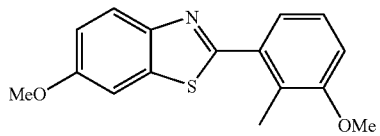

To a solution of 6-methoxy-2-(2-bromo-3-methoxy-phenyl)-benzothiazole (0.128, 0.366 mmol) in dry toluene (4 mL) was added potassium carbonate (0.404 g, 2.92 mmol), methylboronic acid (88 mg, 1.47 mmol) and tetrakis (triphenylphosphine)palladium (42 mg, 0.036 mmol). The mixture was heated to 100° C. for 3 h, then cooled to room temperature. The mixture was diluted with ethylacetate and washed with water, saturated sodium carbonate and brine. After chromatographic purification gave 6-methoxy-2-(2-methyl-3-methoxy-phenyl)-benzothiazole (66 mg, 63% yield) as a white solid. Mass spec: MH$^+$=286.

Example 54

6-Hydroxy-2-(2-methyl-3-hydroxy-phenyl)-benzothiazole

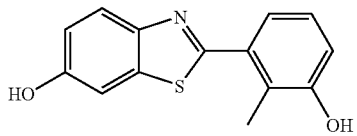

6-Methoxy-2-(2-methyl-3-methoxy-phenyl)-benzothiazole (64 mg, 0.224 mmol) was treated with boron tribroride under standard condition to give 6-hydroxy-2-(2-methyl-3-hydroxy-phenyl)-benzothiazole (52 mg, 90% yield) as a yellow solid. Mass spec: MH$^+$=258.

Example 55

6-Methoxy-2-(3-methoxy-phenyl)-benzothiazole

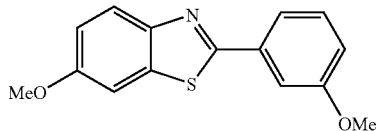

To a solution of 6-methoxy-2-(2-bromo-3-methoxy-phenyl)-benzothiazole (0.182, 0.52 mmol) in dry DMF (3 mL) was added cesium carbonate (0.51 g, 1.57 mmol), triethylborane (0.58 mL, 1M in THF, 0.58 mmol) and 1,1'-bis (diphenylphosphino)ferrocene palladium dichloride dichloromethane (18 mg, 0.022 mmol). The mixture was heated to 50° C. for 24 h, then cooled to room temperature. Saturated sodium bicarbonate was added and the mixture was extracted with ethylacetate. Combined ethylacetate were washed with brine, concentrated. After chromatographic purification gave 6-methoxy-2-(3-methoxy-phenyl)-benzothiazole (54 mg, 38% yield) as a white solid. Mass spec: MH$^+$=272.

Example 56

6-Hydroxy-2-(3-hydroxy-phenyl)-benzothiazole

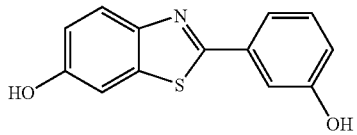

6-Methoxy-2-(3-methoxy-phenyl)-benzothiazole (54 mg, 0.199 mmol) was treated with boron tribromide under standard condition to give 6-hydroxy-2-(3-hydroxy-phenyl)-benzothiazole (15 mg, 31% yield) as a yellow solid. Mass spec: MH$^+$=244.

Example 57

6-Hydroxy-2-(2-R-3-hydroxy-phenyl)-benzothiazole

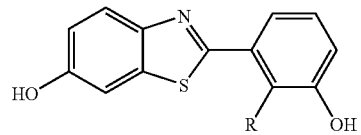

5-Methoxy-2-aminobenzenethiol hydrochloride (1 eq) was dissolved in 1-methyl-2-pyrrolidinone. After triethylamine (1 eq) was added, the mixture was stirred at room temperature for 10 min. 2-R-3-methoxybenzoyl chloride (1 eq) in 1-methyl-2-pyrrolidinone was then added and the mixture was heated at 100° C. (reaction time in the table). The mixture was cooled to room temperature and 1N NaOH was added to PH 9. The mixture was extracted with ethylacetate and combined ethylacetate were washed with brine, concentrated. After chromatographic purification gave 6-methoxy-2-(2-R-3-methoxy-phenyl)-benzothiazole (yield step 1) which was treated with boron tribromide under standard condition to give the title compound (yield step 2).

| R group | —CH$_2$CH$_3$ | —CH(CH$_3$)$_2$ | —C(CH$_2$)(CH$_3$) |
|---|---|---|---|
| Reaction time on step 1 | 45 min | 300 min | 30 min |
| Yield on step 1 | 49 | 25 | 15 |
| Yield on step 2 | 77 | 100 | 43 |
| Mass spec MH$^+$ | 272 | 286 | 284 |

Example 58

4-Cyano-6-methoxy-2-(2-ethyl-3-methoxy-phenyl)-benzothiazole

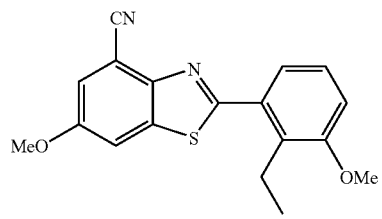

The procedure was the same with 4-cyano-6-methoxy-2-(4-methoxyphenyl)-benzotriazole except using 2-ethyl-3-methoxy-benzoyl chloride instead of p-anisoyl chloride. Mass spec: MH$^+$=325.

Example 59

4-Cyano-6-hydroxy-2-(2-ethyl-3-hydroxy-phenyl)-benzothiazole

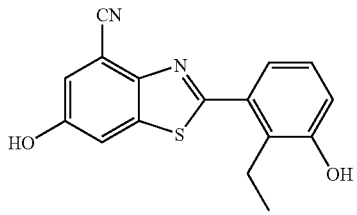

4-Cyano-6-methoxy-2-(2-ethyl-3-methoxy-phenyl)-benzothiazole (0.1 g, 0.31 mmol) was treated with boron tribromide under standard condition to give the title compound (30 mg, 33% yield) as a yellow solid. Mass spec:MH$^+$=297.

Example 60

4-Bromo-6-methoxy-2-(2-isopropyl-3-methoxy-phenyl)-benzothiazole

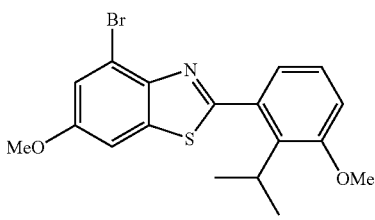

The procedure was the same with 4-bromo-6-methoxy-2-(4-methoxy-phenyl)-benzothiazole except using 2-isopropyl-3-methoxy-benzoyl chloride instead of p-anisoyl chloride. Mass spec: MH$^+$=392.

Example 61

4-Bromo-6-hydroxy-2-(2-isopropyl-3-hydroxy-phenyl)-benzothiazol

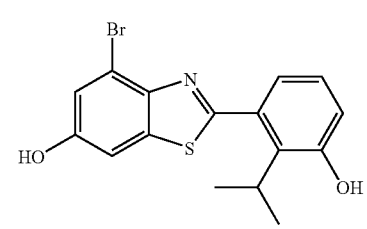

4-Bromo-6-methoxy-2-(2-isopropyl-3-methoxy-phenyl)-benzothiazole (60 mg, 0.153 mmol) was treated with boron tribromide under standard condition to give the title compound (30 mg, 54% yield) as a yellow solid. Mass spec: MH$^+$=364.

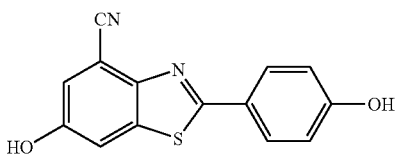

Example 62

4-Cyano-6-hydroxy-2-(4-hydroxy-phenyl)-benzothiazole

4-Cyano-6-methoxy-2-(4-Methoxy-phenyl)-benzothiazole (0.18 g, 0.61 mmol) was suspended in boron tribromide (1M in methylene chloride, 5.0 mL) and stirred at room temp under nitrogen for 18.0 hr. Reaction was poured into aqueous hydrochloric acid (1M). Solid was collected by filtration and washed with water. Washed solid was further purified by flash chromatography on silica affording the title compound (150 mg, 92%) as a yellow solid. MH$^+$=269; $^1$H NMR (300 MHZ, DMSO-d$^6$,) d 10.42(s, 1H), 10.27(s, 1H), 7.91(d, J=8.7 hz, 2H), 7.77(d, J=2.4 hz, 1H), 7.36(d, J=2.4 hz, 1H), 6.94 (d, J=8.4 hz, 2H).

The starting 4-Cyano-6-methoxy-2-(4-Methoxy-phenyl)-benzothiazole was prepared as follows:

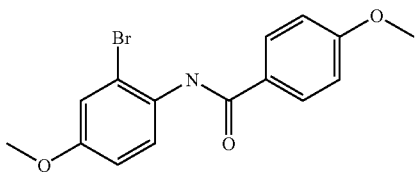

a. N-(2-Bromo-4-Methoxy-phenyl)-4-methoxy-benzamide

To a solution containing 2-bromo-4-methoxy-aniline[1] (3.2 g, 15.8 mmol) in pyridine (25 mL) was added p-anisoyl chloride (2.82 g, 16.5 mmol) dropwise under nitrogen. The reaction was stirred at room temp for 1.0 hr. Reaction was poured cautiously into aqueous 1M hydrochloric acid and extracted with ethyl acetate. Ethyl acetate extracts were washed with: 1) hydrochloric acid (1.0M), 2) saturated brine and concentrated in vacuo. This tan solid was suspended in a solution containing: methanol (10 mL), methylene chloride (30 mL), and ethyl acetate (5 mL), mixed for 5 min, then allowed to sit for 15 min, yielding a white solid. This solid was collected by filtration and dried under vacuum yielding the title compound (1.97 g, 37%) as a white solid. Mass spec: MH$^+$=336.

[1] Prepared following literature procedure: Tet. (56) 2000, 1469

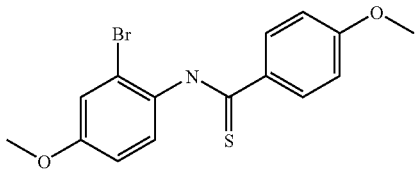

b. N-(2-Bromo-4-Methoxy-phenyl)-4-methoxy-thiobenzamide

N-(2-Bromo-4-Methoxy-phenyl)-4-methoxy-benzamide (1.87 g, 5.6 mmol) and Lawesson's reagent (1.35 g, 3.3 mmol) were suspended in chlorobenzene (15 mL) and heated to reflux under nitrogen for 3.0 hr. Reaction was cooled, solvent removed under vacuum yielding a yellow-orange solid. Solid was dissolved in ethyl acetate and washed with: 1) 1N HCl, 2) saturated brine. Remove solvent under vacuum. Solid was washed with hexane and dried under vacuum yielding the title compound (1.93 g, 98%) as an orange solid. Mass spec: MH$^+$=352.

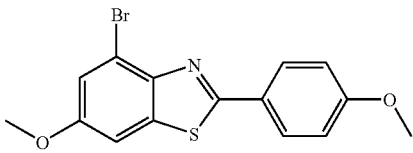

c. 4-Bromo-6-methoxy-2-(4-Methoxy-phenyl)-benzothiazole

N-(2-Bromo-4-Methoxy-phenyl)-4-methoxy-thiobenzamide (1.5 g, 4.25 mmol) was wetted with ethanol (5.0 mL). 30% Aqueous sodium hydroxide (10M, 3.4 mL) was added and stirred for 5 min. Water (6.8 mL) was added to provide a final suspension of 10% aqueous sodium hydroxide. Aliquots (1 mL) of this mixture were added at 1 min intervals to a heated (85° C.) stirred solution containing potassium ferricyanide (5.6 g, 17 mmol) in water (50 mL). Reaction was kept at 85° C. for 30 min, and then cooled to room temp. Cold water (120 mL) was added. Mixture was allowed to sit undisturbed for 30 min. Precipitate was collected by filtration, washed with water, and dried under vacuum. Solid was washed with ether then dried under vacuum at 35° C. yielding the title compound (1.2 g, 80%) as a pale tan solid. Mass spec: MH$^+$=350.

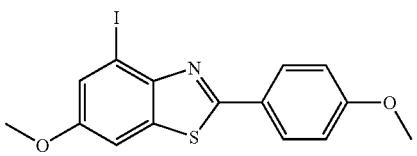

d. 4-Iodo-6-methoxy-2-(4-Methoxy-phenyl)-benzothiazole

4-Bromo-6-methoxy-2-(4-Methoxy-phenyl)-benzothiazole (0.86 g, 2.46 mmol), copper (1) iodide (2.34 g, 12.3 mmol), and potassium iodide (4.08 g, 24.6 mmol) were suspended in DMSO (12 mL) and heated to 175° C. under nitrogen for 4 hr, then cooled to room temp. Reaction was poured cautiously into aqueous hydrochloric acid (1.0M), and extracted with ethyl acetate. Ethyl acetate extracts were washed with: 1) hydrochloric acid (1.0M), 2) saturated sodium thiosulfate, 3) saturated brine and concentrated in vacuo. Solid was washed with methylene chloride/hexane (1:1), dried under vacuum yielding the title compound (0.87 g, 89%) as a pale orange solid MH$^+$=398.

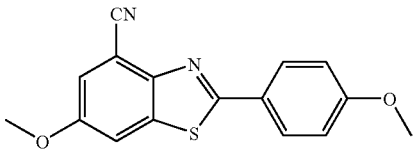

e. 4-Cyano-6-methoxy-2-(4-Methoxy-phenyl)-benzothiazole

4-Iodo-6-methoxy-2-(4-Methoxy-phenyl)-benzothiazole (258 mg, 0.65 mmol) and coppper (1) cyanide (87 mg, 0.975 mmol) were suspended in DMF (6.0 mL) under nitrogen and heated to 150° C. for 2.0 hr then cooled to room temp. Reaction was poured cautiously into aqueous 1M hydrochloric acid and extracted with ethyl acetate. Ethyl acetate extracts were washed with: 1) hydrochloric acid (1.0M), 2) saturated brine and concentrated in vacuo. Solid was washed with ether/hexane (1:2), then dried under vacuum yielding the title compound (0.185 g, 96%) as a pale tan solid. MH$^+$=297

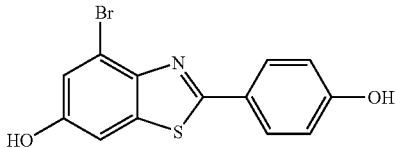

Example 63

4-Bromo-6-hydroxy-2-(4-hydroxy-phenyl)-benzothiazole

4-Bromo-6-methoxy-2-(4-Methoxy-phenyl)-benzothiazole (200 mg, 0.57 mmol) was suspended in boron tribromide (1M in methylene chloride, 7.5 mL) and stirred at room temp under nitrogen for 3.0 hr. Reaction was poured into aqueous hydrochloric acid (1M) and extracted with ethyl acetate. Ethyl acetate extracts were washed with: 1) hydrochloric acid (1.0M), 2) saturated brine and concentrated in vacuo. Washed solid was further purified by flash chromatography on silica affording the title compound (184 mg, 100%) as a yellow solid. MH$^+$=322

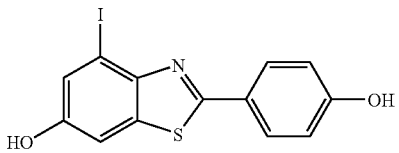

Example 64

4-Iodo-6-hydroxy-2-(4-hydroxy-phenyl)-benzothiazole

4-Iodo-6-methoxy-2-(4-Methoxy-phenyl)-benzothiazole (175 mg, 0.44 mmol) [Compound of Example 1d] was suspended in boron tribromide (1M in methylene chloride, 3.5 mL) and stirred at room temp under nitrogen for 72.0 hr. Reaction was poured into aqueous hydrochloric acid (1M) and extracted with ethyl acetate. Ethyl acetate extracts were washed with: 1) hydrochloric acid (1.0M), 2) saturated brine and concentrated in vacuo. Washed solid was further purified by flash chromatography on silica affording the title compound (158 mg, 97%) as a yellow solid. MH$^+$=370

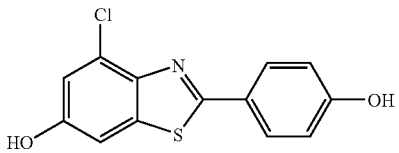

Example 65

4-Chloro-6-hydroxy-2-(4-hydroxy-phenyl)-benzothiazole

4-Chloro-6-methoxy-2-(4-Methoxy-phenyl)-benzothiazole (0.27 g, 0.88 mmol) was suspended in boron tribromide (1M in methylene chloride, 7.0 mL) and stirred at room temp under nitrogen for 18.0 hr. Reaction was poured cautiously into aqueous 1M hydrochloric acid and extracted with ethyl acetate. Ethyl acetate extracts were washed with: 1) hydrochloric acid (1.0M), 2) saturated brine and concentrated in vacuo. Solid was washed with methylene chloride/methanol (97:3, 10 mL), and dried under vacuum yielding the title compound (0.240 g, 98%) as a tan solid. Mass spec: MH$^+$=278

The starting 4-Chloro-6-methoxy-2-(4-Methoxy-phenyl)-benzothiazole was prepared as follows:

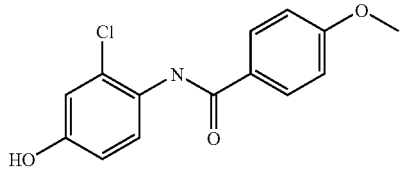

a. N-(2-Chloro-4-hydroxy-phenyl)-4-methoxy-benzamide

To a solution containing 2-chloro-4-hydroxy-aniline hydrochloride(1.44 g, 8 mmol) in pyridine (10 mL) was added p-anisoyl chloride (1.38 g, 8.1 mmol) dropwise under nitrogen. The reaction was stirred at room temp for 1.0 hr. Reaction was poured cautiously into aqueous 1M hydrochloric acid and extracted with ethyl acetate. Ethyl acetate extracts were washed with: 1) hydrochloric acid (1.0M), 2) saturated brine and concentrated in-vacuo. This solid was washed with ether and dried under vacuum yielding the title compound (1.68 g, 76%) as a tan solid Mass spec: MH$^+$=278.

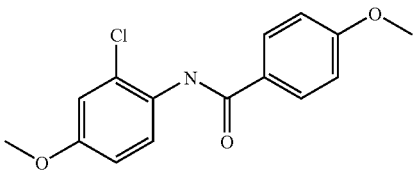

b. N-(2-Chloro-4-methoxy-phenyl)-4-methoxy-benzamide
N-(2-Chloro-4-hydroxy-phenyl)-4-methoxy-benzamide (1.83 g, 6.59 mmol) and potassium carbonate (1.82 g, 13.2 mmol) were suspended in DMF (15 mL). Methyl iodide (0.62 mL, 9.89 mmol) was added and stirred at room temp under nitrogen for 15 min, then heated to 95° C. for 18 hr. Reaction was cooled to room temp then poured cautiously into aqueous 1M hydrochloric acid and extracted with ethyl acetate. Ethyl acetate extracts were washed with: 1) hydrochloric acid (1.0M), 2) saturated NaHCO$_3$, 3) saturated brine and concentrated in vacuo. Washed solid was further purified by flash chromatography on silica affording the title compound (1.31 g, 68%) as a white solid. MH$^+$=292

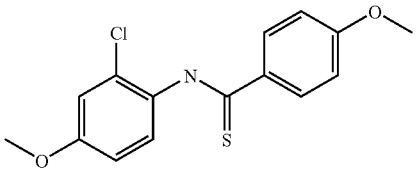

c. N-(2-Chloro-4-methoxy-phenyl)-4-methoxy-thiobenzamide

N-(2-Chloro-4-methoxy-phenyl)-4-methoxy-benzamide (0.62 g, 2.13 mmol) and Lawesson's reagent (0.52 g, 1.28 mmol) were suspended in chlorobenzene (10 mL) and heated to reflux under nitrogen for 3.0 hr. Reaction was cooled, solvent removed under vacuum yielding a yellow-orange solid which was further purified by flash chromatography on silica affording the title compound (0.60 g, 92%) as a yellow solid. Mass spec: MH+=308

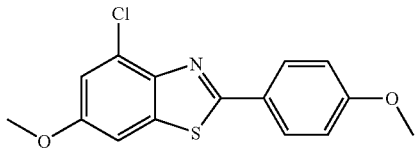

d. 4-Chloro-6-methoxy-2-(4-Methoxy-phenyl)-benzothiazole

N-(2-Chloro-4-Methoxy-phenyl)-4-methoxy-thiobenzamide (0.307 g, 1 mmol) was wetted with ethanol (4.0 mL). 30% Aqueous sodium hydroxide (10M, 0.8 mL) was added and stirred for 5 min. Water (2.4 mL) was added to provide a final suspension of 10% aqueous sodium hydroxide. Aliquots (1 mL) of this mixture were added at 1 min intervals to a heated (85° C.) stirred solution containing potassium ferricyanide (1.32 g, 4 mmol) in water (20 mL). Reaction was kept at 85° C. for 30 min, and then cooled to room temp. Reaction was poured cautiously into aqueous 1M hydrochloric acid and extracted with ethyl acetate. Ethyl acetate extracts were washed with: 1) hydrochloric acid (10M, 2) saturated NaHCO₃, 3) saturated brine and concentrated in vacuo. Solid was washed with ether, dried under vacuum yielding the title compound (0.285 g, 93%) as a white solid. Mass spec: MH+=306

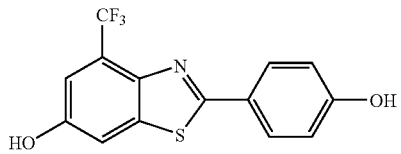

Example 66

2-(4-Hydroxy-phenyl)-4-Trifluormethyl-6-hydroxy-benzothiazole

6-Methoxy-2-(4-Methoxy-phenyl) 4-Trifluoromethyl-benzothiazole (0.08 g, 0.23 mmol) was suspended in boron tribromide (1M in methylene chloride, 5.0 mL) and stirred at room temp under nitrogen for 18.0 hr. Reaction was poured into aqueous hydrochloric acid (1M). Solid was collected by filtration and washed with water. Washed solid was further purified by flash chromatography on silica affording the title compound (21 mg, 29%) as a white solid. MH+=311

The starting 6-Methoxy-2-(4-Methoxy-phenyl) 4-Trifluoromethyl-benzothiazole was prepared as follows:

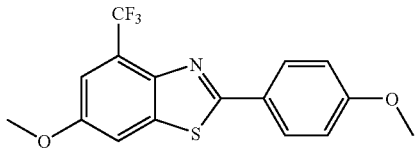

a. 6-Methoxy-2-(4-Methoxy-phenyl) 4-Trifluoromethyl-benzothiazole

4-Iodo-6-methoxy-2-(4-Methoxy-phenyl)-benzothiazole (397 mg, 1.0 mmol) [Compound of Example 1d] and coppper (0) powder (150 mg, 2.36 mmol) were suspended in pyridine (15.0 mL) under nitrogen in a Parr bomb equipped with gas inlet. Trifluoromethyl Iodide (6.0 g, 30.6 mmol) was added via the gas inlet. Reaction was heated to 165° C. for 48.0 hr then cooled to room temp. Remove pyridine under vacuum Reaction was suspended in ethyl acetate/1MHCl (200 mL, 1:1), and filtered. The ethyl acetate extract was washed with: 1) hydrochloric acid (1.0M), 2) saturated NaHCO₃ 3) saturated sodium thiosulfate, 4) saturated brine and concentrated in vacuo. Residue was further purified by flash chromatography on silica affording the title compound (0.16 g, 47%) as a tan solid. Mass spec: MH+=339

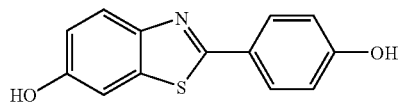

Example 67

2-(4-Hydroxy-phenyl)-6-hydroxy-benzothiazole

6-Methoxy-2-(4-methoxy-phenyl)-benzothiazole (134 mg, 0.49 mmol) and pyridine hydrochloride (1.34 g, 11.6 mmol) were heated to 200° C. under nitrogen for 40 min, and then cooled to room temp. Reaction was poured cautiously into aqueous hydrochloric acid (1M) and extracted with ethyl acetate. Ethyl acetate extracts were washed with: 1) hydrochloric acid (1.0M), 2) saturated brine and concentrated in vacuo. Residue was washed with ether/hexane (1:4), dried under vacuum yielding the title compound (119 mg, 100%) as a yellow solid. MH+=244

The starting 6-Methoxy-2-(4-methoxy-phenyl)-benzothiazole was prepared as follows:

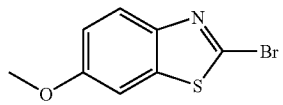

a. 2-Bromo-6-methoxy-benzothiazole

To a solution containing dry Copper (11) bromide (2.68 g, 12 mmol), tri(ethylene glycol) dimethyl ether (5 g) in acetonitrile (150 mL) was added isoamyl nitrite (2 mL, 15 mmol). Reaction was stirred at room temp under nitrogen for 30 min. To this suspension was added, dropwise, a solution (obtained by sonification) containing 2-amino-6-methoxy-benzothiazole (1.8 g, 10 mmol) and tri(ethylene glycol) dimethyl ether (5 g) in acetonitrile (50 mL). Reaction was stirred at room temp for 10 min, and then heated to 50° C. for 3 hr. Reaction was cooled to room temp, poured cautiously into aqueous 6M hydrochloric acid and extracted with ethyl acetate. Ethyl acetate extracts were washed with: 1) hydrochloric acid (1.0M), 2) saturated brine and concentrated in vacuo. Residue was crystallized from ether/hexane (1:10) yielding the title compound (1.48 g, 61%) MH+=244 Supernatant solution was concentrated, dried under vacuum yielding 2,7-dibromo-6-methoxy-benzothiazole (0.45 g, 14%) as a yellow solid. MH+=322

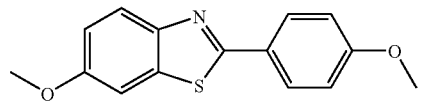

b. 6-Methoxy-2-(4-methoxy-phenyl)-benzothiazole

2-Bromo-6-methoxy-benzothiazole (244 mg, 1 mmol), 4-methoxy-phenyl-boronic acid (198 mg, 1.3 mmol), tetrakis(triphenylphosphine) palladium (0) (58 mg, 0.05 mmol), and cesium fluoride (380 mg, 2.5 mmol) were suspended in acetonitrile (10 mL) and heated to reflux for 90 min under nitrogen. Reaction was cooled to room temp, poured cautiously into aqueous 1M hydrochloric acid and extracted with ethyl acetate. Ethyl acetate extracts were washed with: 1) hydrochloric acid (1.0M), 2) saturated NaHCO$_3$, 3) saturated brine and concentrated in vacuo. Washed solid was further purified by flash chromatography on silica affording the title compound (271 mg, 100%) as a pale yellow solid. MH$^+$=272

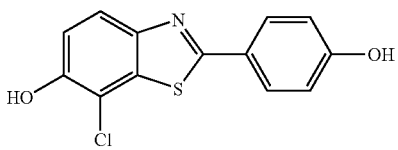

Example 68

7-Chloro-6-hydroxy-2-(4-hydroxy-phenyl)-benzothiazole

7-Bromo-6-methoxy-2-(4-methoxy-phenyl)-benzothiazole (65 mg, 0.186 mmol)) and pyridine hydrochloride (1.6 g, 13.8 mmol) were heated to 200° C. under nitrogen for 45 min; and then cooled to room temp. Reaction was poured cautiously into aqueous 1M hydrochloric acid and extracted with ethyl acetate. Ethyl acetate extracts were washed with: 1) hydrochloric acid (1.0M), 2) saturated brine and concentrated in vacuo. Residue was further purified by flash chromatography on silica affording the title compound (51 mg, 99%) as a white solid. MH$^+$=278

The starting 7-Bromo-6-methoxy-2-(4-methoxy-phenyl)-benzothiazole was prepared as follows:

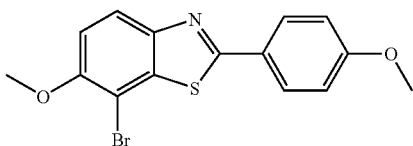

a. 7-Bromo-6-methoxy-2-(4-methoxyphenyl)-benzothiazole 2,7-Dibromo-6-methoxy-benzothiazole (94 mg, 0.29 mmol), 4-methoxy-phenyl-boronic acid (47 mg, 0.31 mmol), tetrakis(triphenylphosphine) palladium (0) (19 mg, 0.015 mmol), and cesium fluoride (110 mg, 0.725 mmol) were suspended in acetonitrile (10 mL) and heated to reflux for 90 min under nitrogen. Reaction was cooled to room temp, poured cautiously into aqueous 1M hydrochloric acid and extracted with ethyl acetate. Ethyl acetate extracts were washed with: 1) hydrochloric acid (1.0M), 2) saturated NaHCO$_3$, 3) saturated brine and concentrated in vacuo. Washed solid was further purified by flash chromatography on silica affording the title compound (71 mg, 70%) as a white solid. MH$^+$=350

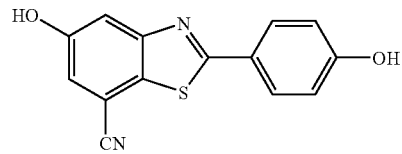

Example 69

7-Cyano-5-hydroxy-2-(4-hydroxy-phenyl)-benzothiazole

5-Methoxy-2-(4-methoxy-phenyl)-benzothiazole-7-carbonitrile (0.04 g, 0.135 mmol) was suspended in boron tribromide (1M in methylene chloride, 5.0 mL) and stirred at room temp under nitrogen for 48 hr. Reaction was poured into aqueous hydrochloric acid (1M) and extracted with ethyl acetate. Ethyl acetate extracts were washed with: 1) hydrochloric acid (1.0M), 2) saturated NaHCO$_3$, 3) saturated brine and concentrated in vacuo. This material was further purified by chromatography on silica yielding the title compound (14 mg, 39%) as a tan solid. Mass spec: MH$^+$=296

5-Methoxy-2-(4-hydroxy-phenyl)-benzothiazole-7-carbonitrile (7 mg, 18%) was also obtained as a white solid from this chromatography.

The starting 7-Cyano-5-Methoxy-2-(4-methoxy-phenyl)-benzothiazole was prepared as follows:

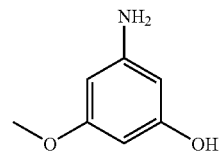

a. 3-Amino-5-methoxy-phenol 3,5 Dimethoxy-aniline (1.53 g, 10 mmol) and pyridine hydrochloride (6.9 g, 60 mmol) were heated to 190° C. under nitrogen for 60 min, and then cooled to room temp. Reaction was poured cautiously into saturated NaHCO$_3$ and extracted with ethyl acetate. Ethyl acetate extracts were washed with: 1) saturated NaHCO$_3$, 2) saturated brine and concentrated in vacuo. Residue was further purified by flash chromatography on silica affording the title compound (600 mg, 44%) as a tan oil. MH$^+$=139

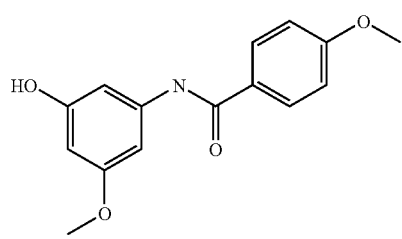

b. N-(3-Hydroxy-5-Methoxy-phenyl)-4-methoxy-benzamide

To a solution containing 3-Amino-5-methoxy-phenol (0.59 g, 4.28 mmol) in pyridine (5 mL) was added p-anisoyl chloride (0.77 g, 4.49 mmol) dropwise under nitrogen. The reaction was stirred at room temp for 18 hr. Reaction was cautiously poured into aqueous 1M hydrochloric acid and extracted with ethyl acetate. Ethyl acetate extracts were washed with: 1) hydrochloric acid (1.0M), 2) saturated brine and concentrated in vacuo. This tan solid was further purified by chromatography on silica yielding the title compound (0.97 g, 83%) as a tan solid. Mass spec. MH+=274.

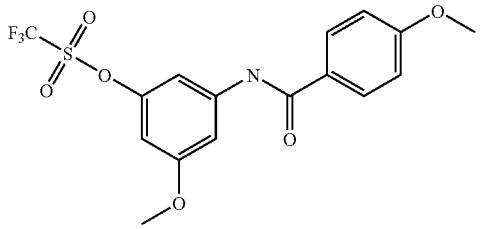

c. Trifluoro-methanesulfonic-acid 3-methoxy-5-(4-methoxy-benzoyl amino)-phenyl ester To a chilled (0° C.) solution containing N-(3-Hydroxy-5-Methoxy-phenyl)-4-methoxy-benzamide (0.546 g, 2 mmol), diisopropylethyl amine (646 mg, 5 mmol) in methylene chloride (15 mL) was added, dropwise, a solution containing triflic anhydride (0.846 g, 3 mmol) in methylene chloride (6 mL) under nitrogen. The reaction was stirred at 0° C. for 10 min and then allowed to warm to room temp for 18 hr. Reaction was poured cautiously into saturated NaHCO₃ and extracted with ethyl acetate. Ethyl acetate extracts were washed with: 1) saturated NaHCO₃, 2) saturated brine and concentrated in vacuo. This material was further purified by chromatography on silica yielding the title compound (0.44 g, 54%) as a tan oil. Mass spec: MH+=406.

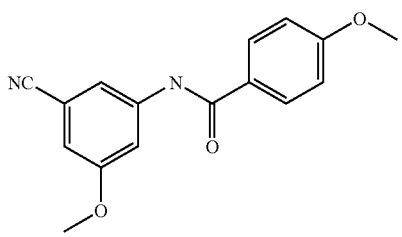

d. N-(3-Cyano-5-methoxy-phenyl)-4-methoxy-benzamide

Trifluoro-methanesulfonic-acid 3-methoxy-5-(4-methoxybenzoyl amino)-phenyl ester (0.41 g, 1 mmol) and potassium cyanide (0.163 g, 2.5 mmol) were suspended in DMF (5 ml) and heated to 120° C. under nitrogen for 18 hr. Reaction was cooled to room temp, poured cautiously into saturated NaHCO₃ and extracted with ethyl acetate. Ethyl acetate extracts were washed with: 1) saturated NaHCO₃, 2) hydrochloric acid (1M), 3) saturated brine and concentrated in vacuo. This material was further purified by chromatography on silica yielding the title compound (0.17 g, 60%) as a tan solid. Mass spec: MH+=283.

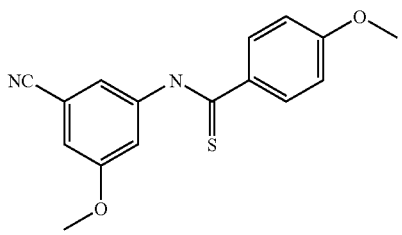

e. N-(3-Cyano-5-methoxy-phenyl)-4-methoxy-thiobenzamide

N-(3-Cyano-5-methoxy-phenyl)-4-methoxy-benzamide (80 mg, 0.28 mmol) and Lawesson's reagent (69 mg, 0.17 mmol) were suspended in chlorobenzene (5 mL) and heated to reflux under nitrogen for 3.0 hr. Reaction was cooled, solvent removed under vacuum. Solid was dissolved in ethyl acetate and washed with: 1) hydrochloric acid (1.0M), 2) saturated NaHCO₃, 3) saturated brine and concentrated in vacuo yielding the title compound (83 mg, 100%) as a yellow-orange solid, Mass spec: MH+=298

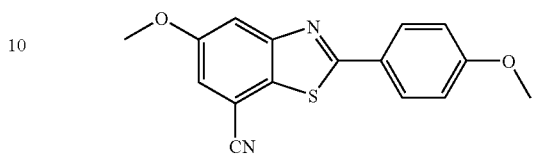

f. 7-Cyano-5-Methoxy-2-(4-methoxy-phenyl)-benzothiazole

N-(3-Cyano-5-methoxy-phenyl)-4-methoxy-thiobenzamide (90 mg, 0.30 mmol) was wetted with ethanol (3.0 mL). 30% Aqueous sodium hydroxide (10M, 2.4 mL) was added and stirred for 5 min. Water (4.8 mL) was added to provide a final suspension of 10% aqueous sodium hydroxide. Aliquots (1 mL) of this mixture were added at 1 min intervals to a heated (85° C.) stirred solution containing potassium ferricyanide (398 mg, 1.21 mmol) in water (6 mL). Reaction was kept at 85° C. for 30 min, and then cooled to room temp. Cold water (120 mL) was added. Extract with ethyl acetate. Ethyl acetate extracts were washed with: 1) hydrochloric acid (1.0M), 2) saturated NaHCO₃, 3) saturated brine and concentrated in vacuo. This material was further purified by chromatography on silica yielding the title compound (44 mg, 49%) as a white solid. Mass spec: MH+=296.

Example 70

2-(4-Amino-phenyl)-6-hydroxy-benzothiazole

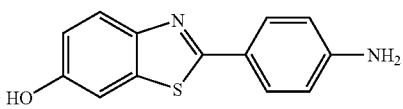

4-(6-Methoxy-benzothiazol-2-yl)-phenylamine (27 mg, 0.105 mmol) was suspended in boron tribromide (1M in methylene chloride, 3.0 mL) and stirred at room temp under nitrogen for 18.0 h. Reaction was poured into saturated NaHCO₃ and extracted with ethyl acetate. Ethyl acetate extracts were washed with: 1) saturated NaHCO₃, 2) saturated brine and concentrated in vacuo. This material was further purified by chromatography on silica yielding the title compound (25 mg, 100%) as a tan solid. Mass spec: MH+=243

The starting 4-(6-Methoxy-benzothiazol-2-yl)-phenylamine was prepared as follows:

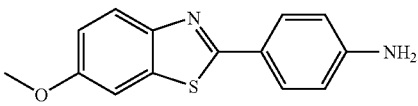

2-Bromo-6-methoxy-benzothiazole (244 mg, 1 mmol) [Example 67], 4-(4,4,5,5-tetramethyl-1,3,2-dioxboralan-2-yl)-aniline (285 mg, 1.3 mmol), tetrakis(triphenylphosphine) palladium (0) (58 mg, 0.05 mmol), and cesium fluoride (380 mg, 2.5 mmol) were suspended in acetonitrile (10 mL) and heated to reflux for 90 min under nitrogen. Reaction was cooled to room temp, poured cautiously into saturated NaHCO₃ and extracted with ethyl acetate. Ethyl acetate extracts were washed with: 1) saturated NaHCO₃, 2) saturated brine and concentrated in vacuo. Washed solid was further purified by flash chromatography on silica affording the title compound (190 mg, 74%) as a pale yellow solid. MH⁺=272

Example 71

6-Bromo-2-(4-hydroxy-phenyl)-benzothiazole

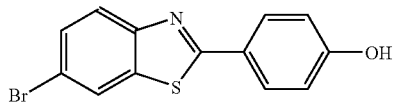

6-Bromo-2-(4-methoxy-phenyl)-benzothiazole (120 mg, 0.375 mmol) was suspended in boron tribromide (1M in methylene chloride, 7.0 mL) and stirred at room temp under nitrogen for 18.0 h. Reaction was poured into saturated brine and extracted with ethyl acetate. Ethyl acetate extracts were washed with: 1) hydrochloric acid (1.0M), 2) saturated brine and concentrated in vacuo. Residue was washed with hexane, and dried under vacuum yielding the title compound (115 mg, 100%) as a tan solid. Mass spec: MH⁺=306

The starting 6-Bromo-2-(4-methoxy-phenyl)-benzothiazole was prepared as follows:

a. N-(4-Bromo-phenyl)-4-methoxy-benzamide
To a solution containing 4-bromo-aniline (1.0 g, 7 mmol) in pyridine (7 mL) was added p-anisoyl chloride (0.77 mL, 7.1 mmol) dropwise under nitrogen. The reaction was stirred at room temp for 30 min. Reaction was poured cautiously into saturated NaHCO₃ and extracted with ethyl acetate. Ethyl acetate extracts were washed with: 1) saturated NaHCO₃, 2) saturated brine and concentrated in vacuo. This solid was washed with a solution containing: ether/hexane (1:5, 10 mL), dried under vacuum, yielding the title compound (1.97 g, 92%) as a white solid. Mass spec: MH⁺=306.

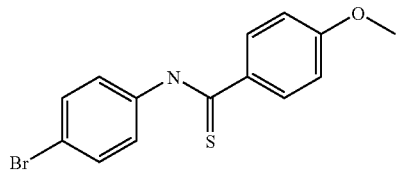

b. N-(4-Bromo-phenyl)-4-methoxy-thiobenzamide
N-(4-Bromo-phenyl)-4-methoxy-benzamide (1.95 g, 6.37 mmol) and Lawesson's reagent (1.55 g, 3.82 mmol) were suspended in chlorobenzene (25 mL) and heated to reflux under nitrogen for 3.0 h. Reaction was cooled, solvent removed under vacuum. Solid was dissolved in ethyl acetate and washed with: 1) hydrochloric acid (1.0M), 2) saturated brine and concentrated in vacuo. Residue was further purified by chromatography on silica yielding the title compound (1.85 g, 90%) as a yellow-orange solid. Mass spec: MH⁺=322

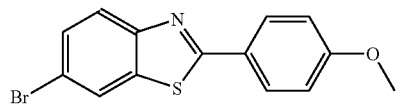

c. 6-Bromo-2-(4-methoxy-phenyl)benzothiazole
N-(4-Bromo-phenyl)-4-methoxy-thiobenzamide (483 mg, 1.5 mmol) was wetted with ethanol (4.0 mL). 30% Aqueous sodium hydroxide (10M, 1.2 mL) was added and stirred for 5 min. Water (2.4 mL) was added to provide a final suspension of 10% aqueous sodium hydroxide. Aliquots (1 mL) of this mixture were added at 1 min intervals to a heated (85° C.) stirred solution containing potassium ferricyanide (1.98 g, 6 mmol) in water (25 mL). Reaction was kept at 85° C. for 30 min, and then cooled to room temp. Cold water (200 mL) was added. Mixture was allowed to sit undisturbed for 30 min. Precipitate was collected by filtration, washed with water, and dried under vacuum. Solid was dried under vacuum at 37° C. yielding the title compound (0.45, 93%) as a pale yellow solid. Mass spec: MH⁺=320.

---

What is claimed is:

1. A compound of the formula (I)

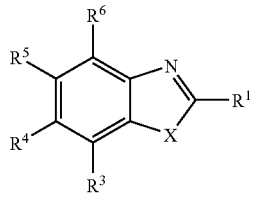

or a pharmaceutically acceptable salt thereof,
wherein:

X is O;

$R^1$ is $C_{1-8}$alkyl, phenyl, wherein the $C_{1-8}$alkyl or phenyl is substituted by 0, 1, 2 or 3 substituents selected from —$R^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro and $C_{1-3}$haloalkyl;

$R^3$ is —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro or $C_{1-3}$haloalkyl; or $R^3$ is $C_{1-3}$alkyl containing 1 or 2 substituents selected from —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano and nitro;

$R^4$ is —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro or $C_{1-3}$haloalkyl;

$R^5$ is —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro or $C_{1-3}$haloalkyl;

$R^6$ is —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro or $C_{1-3}$haloalkyl; or $R^6$ is $C_{1-3}$alkyl containing 1 or 2 substituents selected from —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano and nitro; and $R^a$ is H, $C_{1-6}$alkyl, $C_{1-3}$haloalkyl, phenyl or benzyl, with the provisos that the compound is not methyl-2-(2,6-dichlorophenyl)-1,3-benzoxazole-5-carboxylate or 5-bromomethyl-2-(2,6-dichlorophenyl)-1,3-benzoxazole.

2. The compound of the formula (I) or a pharmaceutically acceptable salt thereof according to claim 1, wherein $R^1$ is unsubstituted or substituted phenyl.

3. The compound of the formula (I) or a pharmaceutically acceptable salt thereof according to claim 1, wherein $R^1$ is halophenyl, $C_{1-4}$alkylphenyl, cyanophenyl or trifluoromethylphenyl.

4. The compound of the formula (I) or a pharmaceutically acceptable salt thereof according to claim 1, wherein $R^3$ is halo, cyano, carbamoyl or $C_{1-6}$alkyl.

5. The compound of the formula (I) or a pharmaceutically acceptable salt thereof according to claim 1, wherein $R^3$ is hydrogen.

6. The compound of the formula (I) or a pharmaceutically acceptable salt thereof according to claim 1, wherein $R^4$ is halo, hydroxy or $C_{1-6}$alkoxy.

7. The compound of the formula (I) or a pharmaceutically acceptable salt thereof according to claim 1, wherein $R^4$ is hydrogen.

8. The compound of the formula (I) or a pharmaceutically acceptable salt thereof according to claim 1, wherein $R^5$ is halo, hydroxy or $C_{1-6}$alkoxy.

9. The compound of the formula (I) or a pharmaceutically acceptable salt thereof according to claim 1, wherein $R^5$ is hydrogen.

10. The compound of the formula (I) or a pharmaceutically acceptable salt thereof according to claim 1, wherein $R^6$ is halo, $C_{1-4}$alkyl, trifluoromethyl, hydroxy, $C_{1-4}$alkoxy, carboxy, $C_{1-4}$alkoxycarbonyl, cyano, halomethyl, cyano$C_{1-4}$alkyl, carbamoyl, methylcarbamoyl or dimethylcarbamoyl.

11. The compound of the formula (I) or a pharmaceutically acceptable salt thereof according to claim 1, wherein $R^6$ is hydrogen.

12. The compound of the formula (I) or a pharmaceutically acceptable salt thereof according to claim 1, wherein $R^3$ is chloro or bromo; $R^5$ is hydroxy; and $R^4$ and $R^6$ are both hydrogen.

13. A pharmaceutical composition comprising a compound of the formula (I) or a pharmaceutically acceptable salt thereof as defined in claim 1 and a pharmaceutically acceptable carrier.

14. A method of treating a disease condition selected from Alzheimer's disease, anxiety disorders, depressive disorders, osteoporosis, cardiovascular disease, rheumatoid arthritis or prostate cancer, which comprises administering an effective amount of a compound of the formula (I) or a pharmaceutically acceptable salt thereof according to claim 18 to a patient in need of such treatment.

15. A process for preparing a compound of the formula (I) or a pharmaceutically acceptable salt thereof, as defined in claim 1 which comprises:

a) cyclizing a compound of the formula:

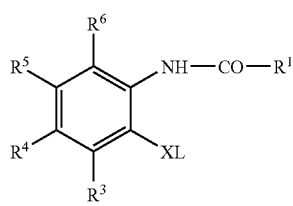

wherein X, R$^1$, and R$^3$–R$^6$ are as defined in claim 18 and L is hydrogen or a leaving group; or b) cyclizing a compound of the formula:

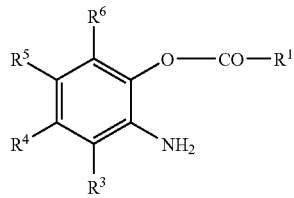

wherein R$^1$ and R$^3$–R$^6$ are as defined in claim 18; or c) cyclizing a compound of the formula:

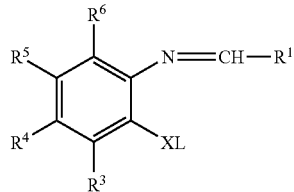

wherein X, R$^1$ and R$^3$–R$^6$ are as defined in claim 18 and L is hydrogen or a leaving group; and thereafter, if desired, forming a pharmaceutically acceptable salt.

* * * * *

SEQUENCE LISTING

```
<160> NUMBER OF SEQ ID NOS: 1

<210> SEQ ID NO 1
<211> LENGTH: 70
<212> TYPE: DNA
<213> ORGANISM: artificial sequence
<220> FEATURE:
<223> OTHER INFORMATION: Synthetic sequence comprising a Vitellogenin-
      gene Estrogen Response Element
<220> FEATURE:
<221> NAME/KEY: misc_feature
<222> LOCATION: (1)..(5)
<223> OTHER INFORMATION: 5/6 bases from 5' end of cleaved Spe I site
<220> FEATURE:
<221> NAME/KEY: misc_feature
<222> LOCATION: (6)..(11)
<223> OTHER INFORMATION: Xho I site
<220> FEATURE:
<221> NAME/KEY: misc_feature
<222> LOCATION: (27)..(32)
```

```
<223> OTHER INFORMATION: Spacer Bgl II site
<220> FEATURE:
<221> NAME/KEY: misc_feature
<222> LOCATION: (70)..(70)
<223> OTHER INFORMATION: 3' overhang C from Afl II cleavage

<400> SEQUENCE: 1
ctagtctcga gaggtcactg tgacctagat ctaggtcact gtgacctaga tctaggtcac      60
tgtgacctac                                                            70
```